(12) United States Patent
Jaeschke et al.

(10) Patent No.: US 9,212,171 B2
(45) Date of Patent: *Dec. 15, 2015

(54) ETHYNYL COMPOUNDS

(71) Applicant: Hoffmann-La Roche Inc., Nutley, NJ (US)

(72) Inventors: Georg Jaeschke, Basel (CH); Synese Jolidon, Blauen (CH); Lothar Lindemann, Basel (CH); Heinz Stadler, Basel (CH); Eric Vieira, Frenkendorf (CH)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/590,530

(22) Filed: Jan. 6, 2015

(65) Prior Publication Data
US 2015/0119384 A1 Apr. 30, 2015

Related U.S. Application Data

(62) Division of application No. 13/452,973, filed on Apr. 23, 2012, now Pat. No. 8,957,213.

(30) Foreign Application Priority Data

Apr. 26, 2011 (EP) .................................. 11163683

(51) Int. Cl.
C07D 401/04 (2006.01)
C07D 401/14 (2006.01)
C07D 403/04 (2006.01)
A61K 31/506 (2006.01)

(52) U.S. Cl.
CPC ............ *C07D 403/04* (2013.01); *A61K 31/506* (2013.01); *C07D 401/04* (2013.01); *C07D 401/14* (2013.01); *Y02T 10/7011* (2013.01)

(58) Field of Classification Search
CPC .. C07D 401/04; C07D 401/14; A61K 31/501; A61K 31/506; A61K 31/4439; A61K 31/444
USPC ............... 544/238, 333, 242; 546/255, 278.4; 514/252.03, 336, 333, 343
See application file for complete search history.

(56) References Cited

U.S. PATENT DOCUMENTS 8,957,213 B2 * 2/2015 Jaeschke et al. ............... 546/255

* cited by examiner

Primary Examiner — Venkataraman Balasubramanian

(57) ABSTRACT

The present invention relates to ethynyl derivatives of formula I

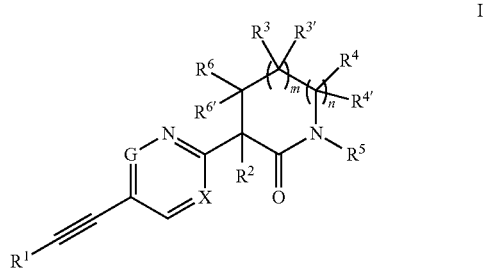

X, G, $R^1$, $R^2$, $R^3$, $R^{3'}$, $R^4$, $R^{4'}$, $R^5$, $R^6$, $R^{6'}$, m, and n are as defined herein or to a pharmaceutically acceptable acid addition salt, to a racemic mixture, or to its corresponding enantiomer and/or optical isomer and/or stereoisomer thereof. Compounds of formula I are positive allosteric modulators (PAM) of the metabotropic glutamate receptor subtype 5 (mGluR5). They can be used for the treatment of schizophrenia or cognitive disorders.

6 Claims, No Drawings

ETHYNYL COMPOUNDS

PRIORITY TO RELATED APPLICATION(S)

This application claims priority to and is a divisional of pending U.S. patent application Ser. No. 13/452,973, filed Apr. 23, 2012, which in turn claims the benefit of European Patent No. 11163683.3, filed Apr. 26, 2011, which all are hereby incorporated by reference in their entireties.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups: mGluR1 and mGluR5 belong to group I, mGluR2 and mGluR3 belong to group II and mGluR4, inGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

A new avenue for developing selective modulators is to identify compounds which act through allosteric mechanism, modulating the receptor by binding to site different from the highly conserved orthosteric binding site. Positive allosteric modulators of mGluR5 have emerged recently as novel pharmaceutical entities offering this attractive alternative. Positive allosteric modulators have been described, for example in WO2008/151184, WO2006/048771, WO2006/129199 and WO2005/044797 and in *Molecular Pharmacology*, 40, 333-336, 1991; *The Journal of Pharmacology and Experimental Therapeutics*, Vol 313, No. 1, 199-206, 2005;

Positive allosteric modulators are compounds that do not directly activate receptors by themselves, but markedly potentiate agonist-stimulated responses, increase potency and maximum of efficacy. The binding of these compounds increase the affinity of a glutamate-site agonist at its extracellular N-terminal binding site. Positive allosteric modulation is thus an attractive mechanism for enhancing appropriate physiological receptor activation. There is a scarcity of selective positive allosteric modulators for the mGluR5 receptor. Conventional mGluR5 receptor modulators typically lack satisfactory aqueous solubility and exhibit poor oral bioavailability. Therefore, there remains a need for compounds that overcome these deficiencies and that effectively provide selective positive allosteric modulators for the mGluR5 receptor.

SUMMARY OF THE INVENTION

The present invention provides ethynyl compounds of formula I

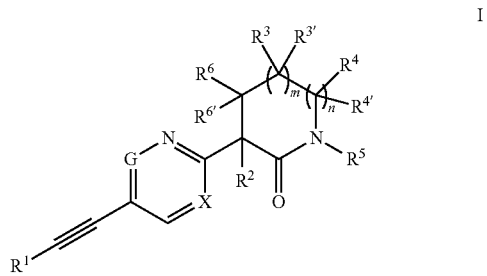

wherein

X is N or C—R, wherein R is hydrogen or halogen;

G is N or CH;

with the proviso that only one of G or X is nitrogen;

$R^1$ is phenyl or pyridinyl, each of which is optionally substituted by halogen;

$R^2$ is hydrogen, lower alkyl, hydroxy, lower alkoxy or C(O)O-benzyl;

$R^3$, $R^{3'}$, $R^4$, $R^{4'}$, $R^6$, and $R^{6'}$ are each independently hydrogen or lower alkyl;

or $R^6$ and $R^4$ together with the carbon atom to which they are attached form a $C_{4-6}$-cycloalkyl ring, when m is 0 and n is 1 or 2;

$R^5$ is hydrogen or lower alkyl;

n is 0, 1 or 2; and m is 0 or 1; with the proviso that n and m are not simultaneously 0;

or a pharmaceutically acceptable acid addition salt, to a racemic mixture, or its corresponding enantiomer and/or optical isomer and/or stereoisomer thereof.

Compounds of formula I are positive allosteric modulators (PAM) of the metabotropic glutamate receptor subtype 5 (mGluR5).

Compounds of formula I are distinguished by having valuable therapeutic properties. They can be used in the treatment or prevention of disorders, relating to positive allosteric modulators for the mGluR5 receptor.

The most preferred indications for compounds which are positive allosteric modulators are schizophrenia and cognition.

The present invention provides compounds of formula I and their pharmaceutically acceptable salts, pharmaceutical compositions containing them, processes for their production, and methods for the treatment or prevention of disorders relating to positive allosteric modulators for the mGluR5 receptor, such as schizophrenia, tuberous sclerosis, and cognition by administering them.

DETAILED DESCRIPTION OF THE INVENTION

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "lower alkoxy" denotes a group —O—R' wherein R' is lower alkyl as defined above.

The term "halogen" denotes fluoro, chloro, bromo or iodo.

The term "$C_{3-6}$-cycloalkyl" denotes a monovalent saturated monocyclic hydrocarbon group of 3 to 6 ring carbon atoms. Particular cycloalkyl groups are, for example, cyclopropyl, cyclobutanyl, cyclopentyl, and cyclohexyl.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgment of the attending medical or veterinary practitioner, and other factors.

One embodiment of the invention are compounds of formula IA

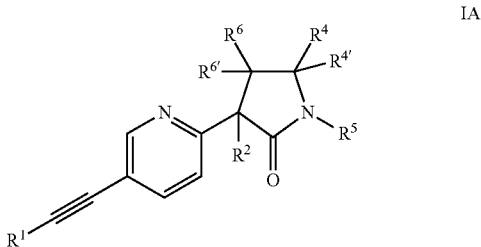

wherein
$R^1$ is phenyl or pyridinyl, each of which is optionally substituted by halogen;
$R^2$ is hydrogen, lower alkyl, hydroxy, lower alkoxy or C(O)O-benzyl;
$R^4$, $R^{4'}$, $R^6$, and $R^{6'}$ are each independently hydrogen or lower alkyl;
or $R^6$ and $R^4$ together with the carbon atom to which they are attached form a $C_{4-6}$-cycloalkyl ring; and
$R^5$ is hydrogen or lower alkyl;
or a pharmaceutically acceptable acid addition salt, a racemic mixture, or its corresponding enantiomer and/or optical isomer and/or stereoisomer thereof.

Examples from this group of compounds are
(RS)-1,5,5-trimethyl-3-(5-(phenylethynyl)pyridin-2-yl)pyrrolidin-2-one;
(RS)-1,5,5-trimethyl-3-(5-(pyridin-3-ylethynyl)pyridin-2-yl)pyrrolidin-2-one;
(RS)-3-(5-((3-chloropheny)ethynyl)pyridin-2-yl)-1,5,5-trimethylpyrrolidin-2-one;
(RS)-3-(5-((3-fluorophenylethynyl)pyridin-2-yl)-1,5,5-trimethylpyrrolidin-2-one;
(RS)-3-hydroxy-1,5,5-trimethyl-3-(5-(phenylethynyl)pyridin-2-yl)pyrrolidin-2-one;
(RS)-3-methoxy-1,5,5-trimethyl-3-(5-(phenylethynyl)pyridin-2-yl)pyrrolidin-2-one;
(RS)-1,3,5,5-tetramethyl-3-(5-(phenylethynyl)pyridin-2-yl)pyrrolidin-2-one;
(3RS,3aSR,6aSR)-1-methyl-3-(5-phenylethynyl-pyridin-2-yl)-hexahydro-cyclopenta[b]pyrrol-2-one;
(3R,3aS,6aS) or (3S,3aR,6aR)-1-methyl-3-(5-phenylethynyl-pyridin-2-yl)-hexahydro-cyclopenta[b]pyrrol-2-one;
(3RS,3aSR,6aSR)-3-[5-(4-fluoro-phenylethynyl)-pyridin-2-yl]-1-methyl-hexahydro-cyclopenta[b]pyrrol-2-one;
(3RS,3aSR,6aSR)-3-[5-(3-fluoro-phenylethynyl)-pyridin-2-yl]-1-methyl-hexahydro-cyclopenta[b]pyrrol-2-one;
(3R,3aS,6aS) or (3S,3aR,6aR)-3-[5-(3-fluoro-phenylethynyl)-pyridin-2-yl]-1-methyl-hexahydro-cyclopenta[b]pyrrol-2-one;
(3R,3aR,6aR) or (3R,3aS,6aS)-3-[5-(3-fluoro-phenylethynyl)-pyridin-2-yl]-1-methyl-hexahydro-cyclopenta[b]pyrrol-2-one;
(3RS,6SR,7SR)-1-methyl-3-(5-phenylethynyl-pyridin-2-yl)-octahydro-indol-2-one;
(3SR,6SR,7SR)-1-methyl-3-(5-phenylethynyl-pyridin-2-yl)-2-one;
(3R,6S,7S)-1-methyl-3-(5-phenylethynyl-pyridin-2-yl)-octahydro-indol-2-one and (3S,6R,7R)-1-Methyl-3-(5-phenylethynyl-pyridin-2-yl)-octahydro-indol-2-one;
(3RS,6SR,7SR)-3-[5-(3-fluoro-phenylethynyl)-pyridin-2-yl]-1-methyl-octahydro-indol-2-one;
(3SR,6SR,7SR)-3-[5-(3-fluoro-phenylethynyl)-pyridin-2-yl]-1-methyl-octahydro-indol-2-one;
(3R,6S,7S)-3-[5-(3-fluoro-phenylethynyl)-pyridin-2-yl]-1-methyl-octahydro-indol-2-one;

(3S,6R,7R)-3-[5-(3-fluoro-phenylethynyl)-pyridin-2-yl]-1-methyl-octahydro-indol-2-one;
(3R,6S,7S)-3-[5-(4-fluoro-phenylethynyl)-pyridin-2-yl]-1-methyl-octahydro-indol-2-one;
(3S,6R,7R)-3-[5-(4-fluoro-phenylethynyl)-pyridin-2-yl]-1-methyl-octahydro-indol-2-one;
(RS)-3-[5-(2-chloro-pyridin-4-ylethynyl)-pyridin-2-yl]-1,5,5-trimethyl-pyrrolidin-2-one;
(S) or (R)-3-[5-(2-chloro-pyridin-4-ylethynyl)-pyridin-2-yl]-1,5,5-trimethyl-pyrrolidin-2-one; and
(R) or (S)-3-[5-(2-chloro-pyridin-4-ylethynyl)-pyridin-2-yl]-1,5,5-trimethyl-pyrrolidin-2-one.

One embodiment of the invention are compounds of formula IB

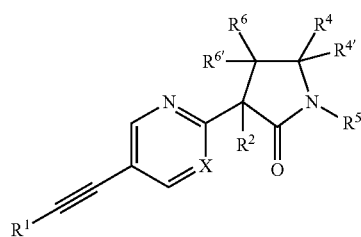

IB wherein
X is N or C—R, wherein R is halogen;
$R^1$ is phenyl or pyridinyl, each of which is optionally substituted by halogen;
$R^2$ is hydrogen, lower alkyl, hydroxy, lower alkoxy or C(O)O-benzyl;
$R^4$, $R^{4'}$, $R^6$, and $R^{6'}$ are each independently hydrogen or lower alkyl;
or $R^6$ and $R^4$ together with the carbon atom to which they are attached form a $C_{4-6}$-cycloalkyl ring; and
$R^5$ is hydrogen or lower alkyl;
or a pharmaceutically acceptable acid addition salt, a racemic mixture, or its corresponding enantiomer and/or optical isomer and/or stereoisomer thereof.

Examples from this group of compounds are
(RS)-benzyl 1,5,5-trimethyl-2-oxo-3-(5-(phenylethynyl)pyrimidin-2-yl)pyrrolidine-3-carboxylate;
(RS)-1,5,5-trimethyl-3-(5-(phenylethynyl)pyrimidin-2-yl)pyrrolidin-2-one;
(RS)-3-(5-((3-fluorophenylethynyl)pyrimidin-2-yl)-1,5,5-trimethylpyrrolidin-2-one;
(RS)-3-(5-((4-fluorophenylethynyl)pyrimidin-2-yl)-1,5,5-trimethylpyrolidin-2-one; and
(3RS,3aSR,6aSR)-1-methyl-3-(5-phenylethynyl-pyrimidin-2-yl)-hexahydro-cyclopenta[b]pyrrol-2-one.

One embodiment of the invention are compounds of formula IC

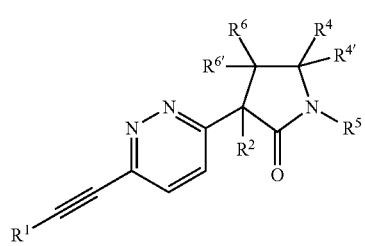

IC wherein
$R^1$ is phenyl or pyridinyl, each of which is optionally substituted by halogen;
$R^2$ is hydrogen, lower alkyl, hydroxy, lower alkoxy or C(O)O-benzyl;
$R^4$, $R^{4'}$, $R^6$, and $R^{6'}$ are each independently hydrogen or lower alkyl;
or $R^6$ and $R^4$ together with the carbon atom to which they are attached form a $C_{4-6}$-cycloalkyl ring; and
$R^5$ is hydrogen or lower alkyl;
or a pharmaceutically acceptable acid addition salt, a racemic mixture, or its corresponding enantiomer and/or optical isomer and/or stereoisomer thereof.

Examples from this group of compounds are
(RS)-3-(6-((3-fluoropheny)ethynyl)pyridazin-3-yl)-1,5,5-trimethylpyrrolidin-2-one;
(RS)-3-(6-((4-fluorophenyl)ethynyl)pridazin-3-yl)-1,5,5-trimethylpyrrolidin-2-one; and
(RS)-3-(6-(phenylethynyl)pyridazin-3-yl)-1,5,5-trimethylpyrrolidin-2-one.

One embodiment of the invention are compounds of formula ID

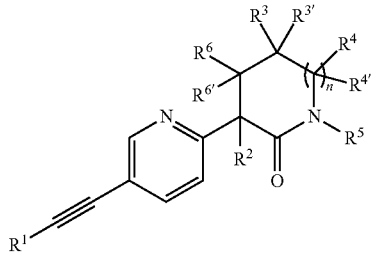

ID wherein
$R^1$ is phenyl or pyridinyl, each of which is optionally substituted by halogen;
$R^2$ is hydrogen, lower alkyl, hydroxy, lower alkoxy or C(O)O-benzyl;
$R^3$, $R^{3'}$, $R^4$, $R^{4'}$, $R^6$, and $R^{6'}$ are each independently hydrogen or lower alkyl;
$R^5$ is hydrogen or lower alkyl; and
n is 1 or 2;
or a pharmaceutically acceptable acid addition salt, a racemic mixture, or its corresponding enantiomer and/or optical isomer and/or stereoisomer thereof.

Examples from this group of compounds are
(RS)-1,6,6-trimethyl-3-(5-(phenylethynyl)pyridin-2-yl)piperidin-2-one;
(RS)-3-(5-((3-fluorophenylethynyl)pyridin-2-yl)-1,6,6-trimethylpiperidin-2-one;
(RS)-3-(5-((4-fluoropheny)ethynyl)pyridin-2-yl)-1,6,6-trimethylpiperidin-2-one;
(RS)-1-methyl-3-(5-phenylethynyl-pyridin-2-yl)-azepan-2-one;
(RS)-3-[5-(4-fluoro-phenylethynyl)-pyridin-2-yl]-1-methyl-azepan-2-one;
(RS)-3-[5-(3-fluoro-phenylethynyl)-pyridin-2-yl]-1-methyl -azepan-2-one;
(S or R)-1-methyl-3-(5-phenylethynyl-pyridin-2-yl)-azepan-2-one; and
(R or S)-1-methyl-3-(5-phenylethynyl-pyridin-2-yl)-azepan-2-one.

One embodiment of the invention are compounds of formula IE

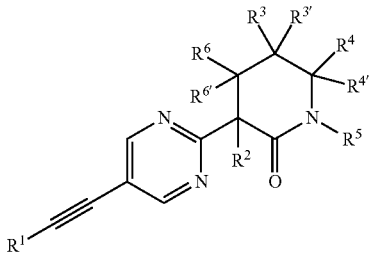

wherein
R¹ is phenyl or pyridinyl, each of which is optionally substituted by halogen;
R² is hydrogen, lower alkyl, hydroxy, lower alkoxy or C(O)O-benzyl;
R³, R³', R⁴, R⁴', R⁶, and R⁶' are each independently hydrogen or lower alkyl; and
R⁵ is hydrogen or lower alkyl;
or a pharmaceutically acceptable acid addition salt, a racemic mixture, or its corresponding enantiomer and/or optical isomer and/or stereoisomer thereof.
Examples from this group of compounds are
(RS)-1,6,6-trimethyl-3-(5-(phenylethynyl)pyrimidin-2-yl)piperidin-2-one;
(RS)-3-(5-((4-fluorophenyl)ethynyl)pyrimidin-2-yl)-1,6,6-trimethylpiperidin-2-one; and
(RS)-3-(5-(3-fluoropheny)ethynyl)pyrimidin-2-yl)-1,6,6-trimethylpiperidin-2-one.
A further embodiment of the invention are compounds of formula I-1

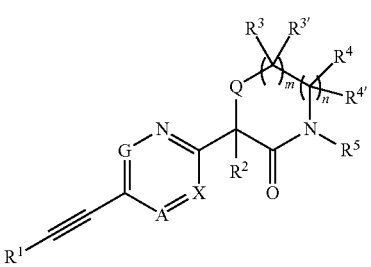

wherein
X is N or C—R, wherein R is hydrogen, methyl or halogen;
G and A are independently N or CH;
  with the proviso that only one of G, A or X is nitrogen;
Q is O, N—R⁹ or —CR⁶R⁶'—;
R¹ is phenyl or heteroaryl, each of which is optionally substituted by halogen, lower alkyl or lower alkoxy;
R² is hydrogen, lower alkyl, hydroxy, lower alkoxy, C(O)O-benzyl, C(O)O-lower alkyl or CONR⁷R⁸;
R³, R³', R⁴, R⁴', R⁶, and R⁶' are each independently hydrogen, lower alkyl, alkoxy, hydroxy or CH₂-lower alkoxy;
  or R³ and R⁴ together with the carbon atom to which they are attached form a C₄₋₆-cycloalkyl ring;
R⁵ is hydrogen, lower alkyl, or together with R⁴ form a C₃-C₆-cycloalkyl;
R⁷ and R⁸ are each independently hydrogen or lower alkyl, or R⁷ together with R⁸ forms a C₃-C₆-cycloalkyl ring;
R⁹ is hydrogen or lower alkyl;
n is 0, 1 or 2; and
m is 0 or 1;
or a pharmaceutically acceptable acid addition salt, a racemic mixture, or its corresponding enantiomer and/or optical isomer and/or stereoisomer thereof.

The preparation of compounds of formula 1 of the present invention can be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process variants described below, which process comprises
a) reacting a compound of formula

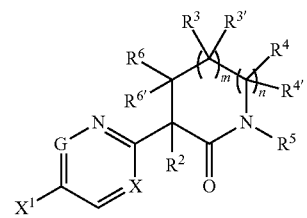

wherein X¹ is halogen
with a compound of formula

to form a compound of formula

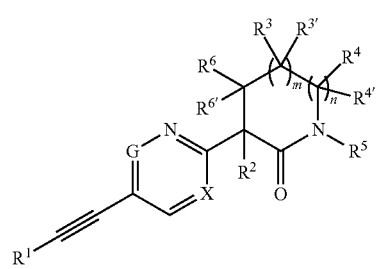

wherein the definitions are as described above or
b) reacting a compound of formula

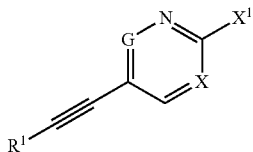

wherein $X^1$ is halogen
with a compound of formula

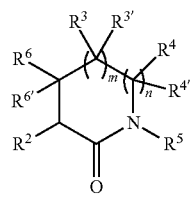

to form a compound of formula

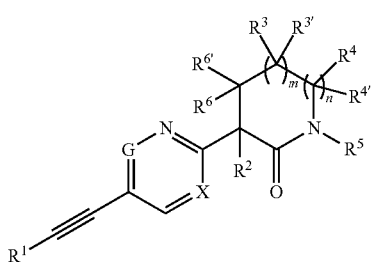

I wherein the definitions are as described above, or, if desired, converting the compounds obtained into pharmaceutically acceptable acid addition salts.

The preparation of compounds of formula I is further described in more detail in schemes 1 to 4 and in examples 1-46.

Scheme 1

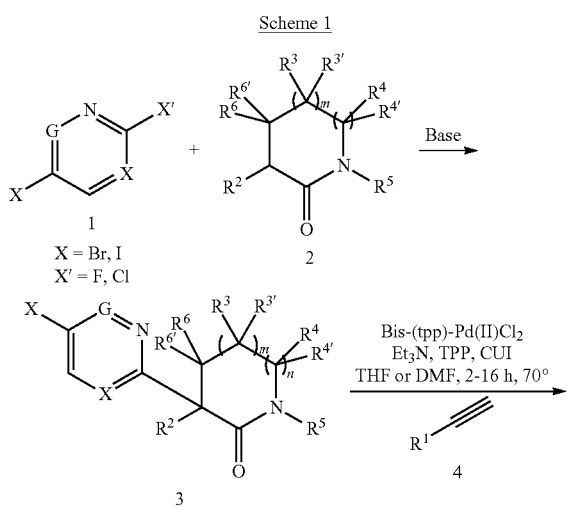

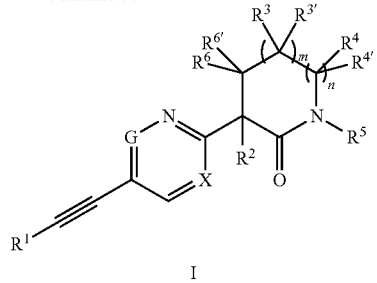

I

An acetylenic compound of formula I can be obtained for example by reaction of a para-dihalo disubstituted heterocyclic derivative 1 with an appropriately substituted cyclic amide 2 in the presence of a strong base such as sodium hydride, sodium hexamethyldisilylamide (NaHMDS), lithium diisopropylamide (LDA), or in an inert solvent like toluene, DMF, DMSO or THF; or sodium alkoxide in a corresponding alcohol as solvent to form the corresponding 3-heteroaryl lactam derivatives 3. Sonogashira coupling of the lactams 3 with an appropriately substituted arylacetylene 4 yield the desired ethynyl compounds of formula I (scheme 1).

Scheme 2

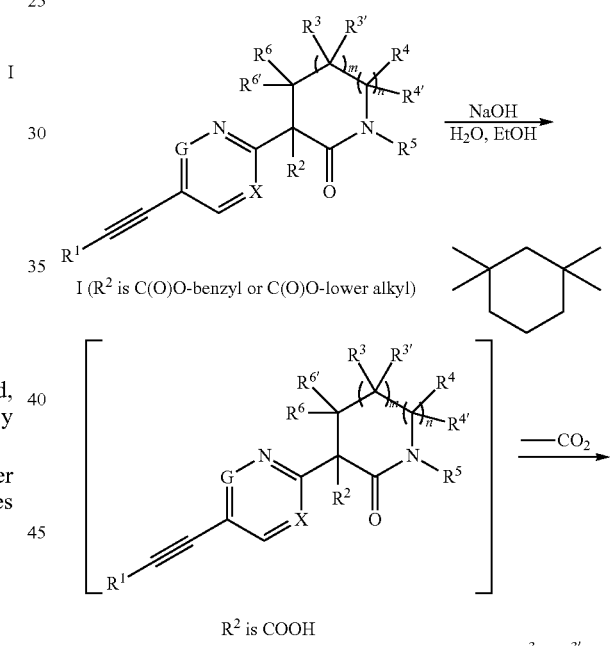

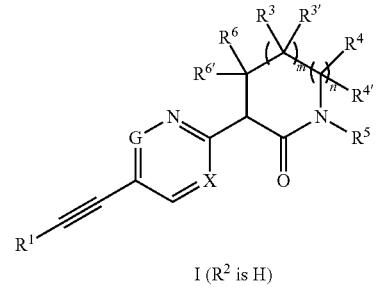

I ($R^2$ is H)

An acetylenic compound of formula I can be obtained for example when $R^2$=COO-benzyl or COO-lower alkyl by hydrolysis of the ester group using for example, aqueous sodium of potassium hydroxide in a solvent such as methanol or ethanol followed by decarboxylation of the acid formed to yield a compound of formula I where $R^2$ is hydrogen (scheme 2).

Scheme 3

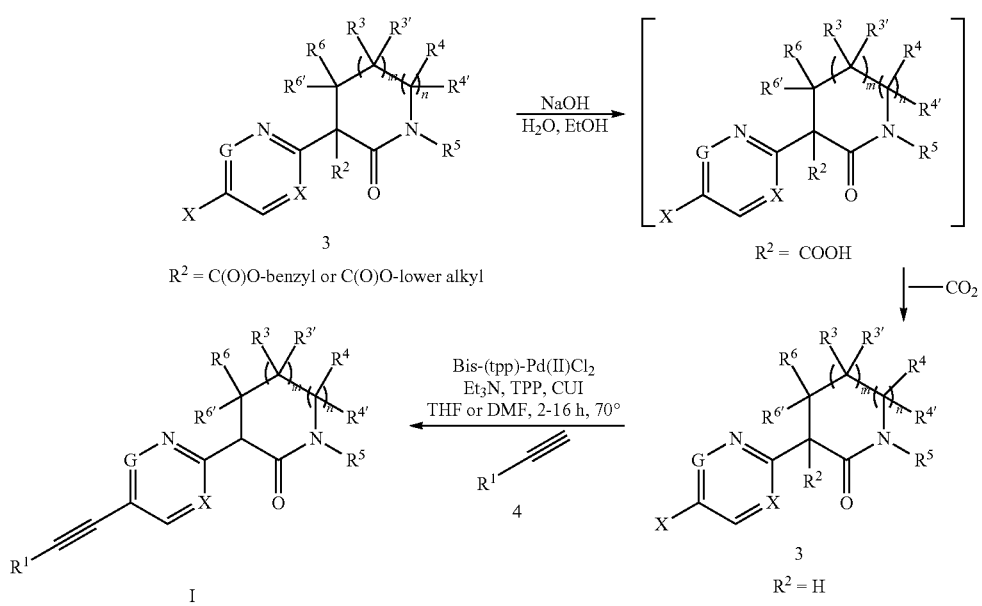

The latter procedure can also be used to modify a compound of formula 3 where $R^2$ is an ester to form a compound of formula 3 where $R^2$ is hydrogen. Sonogashira coupling of the lactams 3 with appropriately substituted arylacetylenes 4 yield the desired ethynyl compounds of formula I where $R^2$ is hydrogen (scheme 3).

Scheme 4

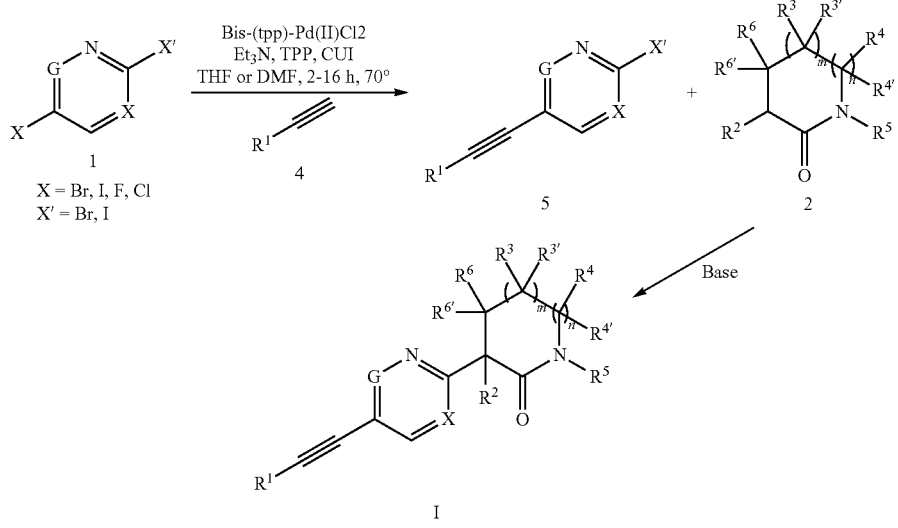

Formula I can also be modified in certain cases, for example by first running the Sonogashira coupling to form an appropriately substituted aryl- or heteroaryl-ethynyl derivative 5 followed by reaction with a lactam of formula 2 using procedures similar to those described in schemes 1 to 3 (scheme 4).

Biological Assay and Data

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 mg/ml hygromycin and 15 µg/ml blasticidin (all cell culture reagents and antibiotics from Invitrogen, Basel, Switzerland).

About 24 hrs before an experiment, $5\times10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist L-glutamate was added to the cells at a concentration corresponding to $EC_{20}$ (typically around 80 μM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was $y=A+((B-A)/(1+((x/C)^D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the table below are shown the prepared compounds 1-46 with corresponding results ($EC_{50}$ in nM).

LIST OF EXAMPLES

| Ex. | Structure | Name | $EC_{50}$ (nM) mGlu5 PAM | Eff. (%) |
|---|---|---|---|---|
| 1 | 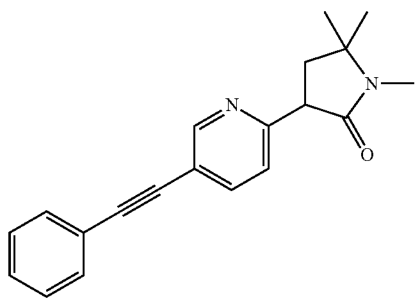 [SMILES: CN1C(=O)C(c2ccc(C#Cc3ccccc3)cn2)CC1(C)C] | (RS)-1,5,5-trimethyl-3-(5-(phenylethynyl)pyridin-2-yl)pyrrolidin-2-one | 60 | 111 |
| 2 | 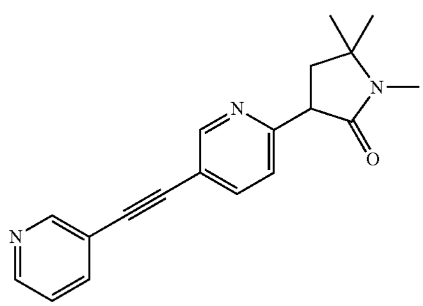 [SMILES: CN1C(=O)C(c2ccc(C#Cc3cccnc3)cn2)CC1(C)C] | (RS)-1,5,5-trimethyl-3-(5-(pyridin-3-ylethynyl)pyridin-2-yl)pyrrolidin-2-one | 981 | 107 |
| 3 | 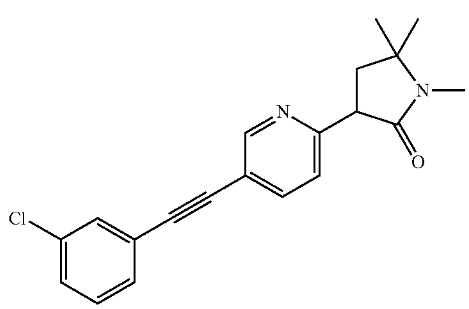 | (RS)-3-(5-((3-chlorophenyl)ethynyl)pyridin-2-yl)-1,5,5-trimethylpyrrolidin-2-one | 38 | 81 |

-continued

| Ex. | Structure | Name | EC₅₀ (nM) mGlu5 PAM | Eff. (%) |
|---|---|---|---|---|
| 4 | 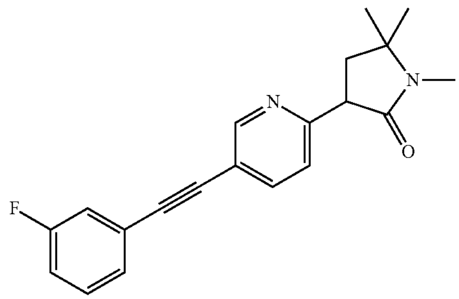 [SMILES: CN1C(=O)C(c2ccc(C#Cc3cccc(F)c3)cn2)CC1(C)C] | (RS)-3-(5-((3-fluorophenyl)ethynyl)pyridin-2-yl)-1,5,5-trimethylpyrrolidin-2-one | 61 | 103 |
| 5 | 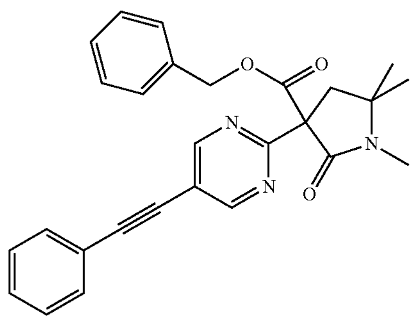 [SMILES: CN1C(=O)C(C(=O)OCc2ccccc2)(c2ncc(C#Cc3ccccc3)cn2)CC1(C)C] | (RS)-benzyl 1,5,5-trimethyl-2-oxo-3-(5-(phenylethynyl)pyrimidin-2-yl)pyrrolidine-3-carboxylate | 528 | 48 |
| 6 | 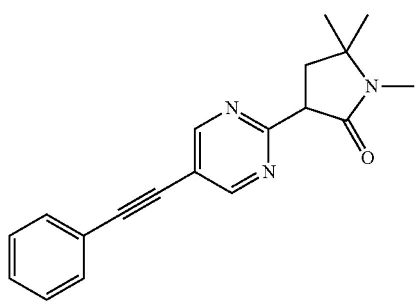 [SMILES: CN1C(=O)C(c2ncc(C#Cc3ccccc3)cn2)CC1(C)C] | (RS)-1,5,5-trimethyl-3-(5-(phenylethynyl)pyrimidin-2-yl)pyrrolidin-2-one | 130 | 90 |
| 7 | 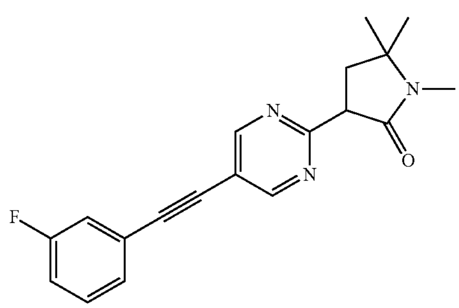 [SMILES: CN1C(=O)C(c2ncc(C#Cc3cccc(F)c3)cn2)CC1(C)C] | (RS)-3-(5-((3-fluorophenyl)ethynyl)pyrimidin-2-yl)-1,5,5-trimethylpyrrolidin-2-one | 137 | 85 |
| 8 | 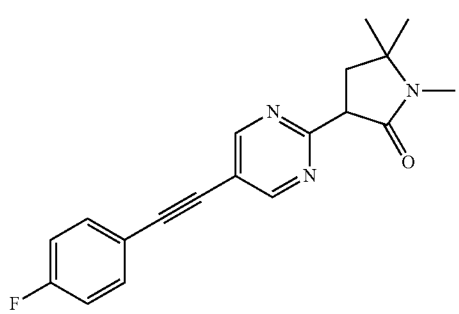 [SMILES: CN1C(=O)C(c2ncc(C#Cc3ccc(F)cc3)cn2)CC1(C)C] | 3-(5-((4-fluorophenyl)ethynyl)pyrimidin-2-yl)-1,5,5-trimethylpyrrolidin-2-one | 390 | 105 |

-continued

| Ex. | Structure | Name | EC$_{50}$ (nM) mGlu5 PAM | Eff. (%) |
|---|---|---|---|---|
| 9 | 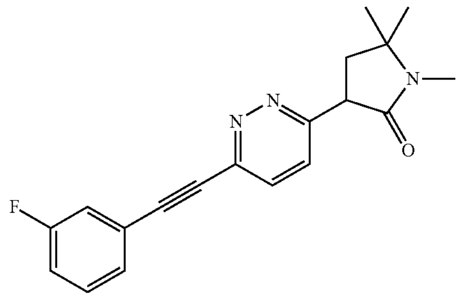 [SMILES: CN1C(=O)C(c2ccc(C#Cc3cccc(F)c3)nn2)CC1(C)C] | 3-(6-((3-fluorophenyl)ethynyl)pyridazin-3-yl)-1,5,5-trimethylpyrrolidin-2-one | 34 | 88 |
| 10 | 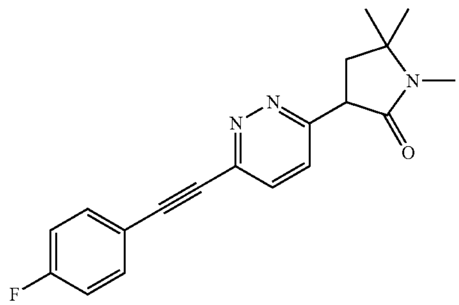 [SMILES: CN1C(=O)C(c2ccc(C#Cc3ccc(F)cc3)nn2)CC1(C)C] | 3-(6-((4-fluorophenyl)ethynyl)pyridazin-3-yl)-1,5,5-trimethylpyrrolidin-2-one | 247 | 99 |
| 11 | 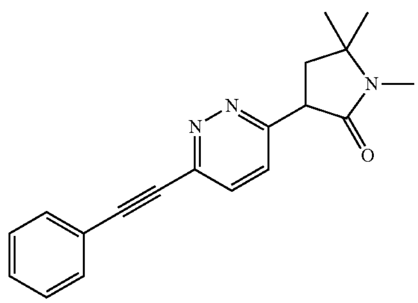 [SMILES: CN1C(=O)C(c2ccc(C#Cc3ccccc3)nn2)CC1(C)C] | (RS)-1,5,5-trimethyl-3-(6-(phenylethynyl)pyridazin-3-yl)pyrrolidin-2-one | 58 | 115 |
| 12 | 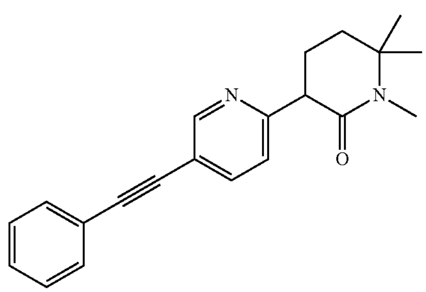 [SMILES: CN1C(=O)C(c2ccc(C#Cc3ccccc3)cn2)CCC1(C)C] | (RS)-1,6,6-trimethyl-3-(5-(phenylethynyl)pyridin-2-yl)piperidin-2-one | 113 | 103 |
| 13 | 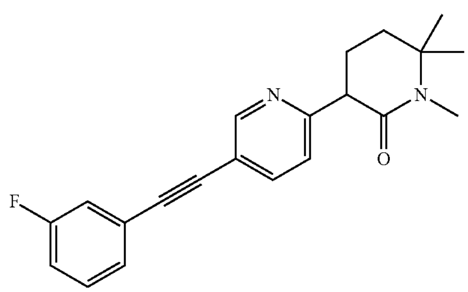 [SMILES: CN1C(=O)C(c2ccc(C#Cc3cccc(F)c3)cn2)CCC1(C)C] | (RS)-3-(5-((3-fluorophenyl)ethynyl)pyridin-2-yl)-1,6,6-trimethylpiperidin-2-one | 98 | 90 |

-continued

| Ex. | Structure | Name | EC$_{50}$ (nM) mGlu5 PAM | Eff. (%) |
|---|---|---|---|---|
| 14 | 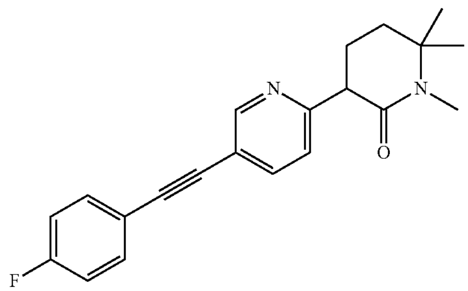 | (RS)-3-(5-((4-fluorophenyl)ethynyl)pyridin-2-yl)-1,6,6-trimethylpiperidin-2-one | 212 | 96 |
| 15 | 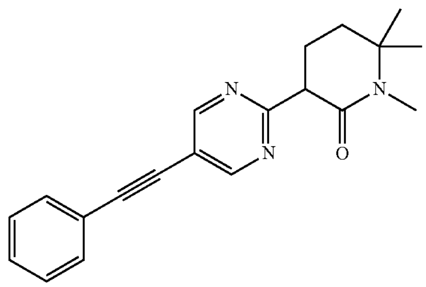 | (RS)-1,6,6-trimethyl-3-(5-(phenylethynyl)pyrimidin-2-yl)piperidin-2-one | 179 | 91 |
| 16 | 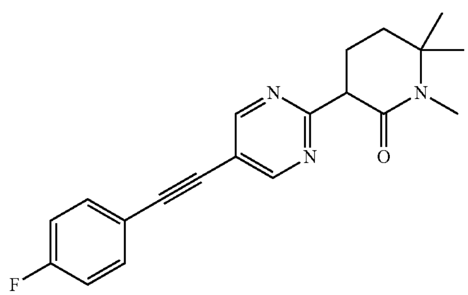 | (RS)-3-(5-((4-fluorophenyl)ethynyl)pyrimidin-2-yl)-1,6,6-trimethylpiperidin-2-one | 573 | 96 |
| 17 | 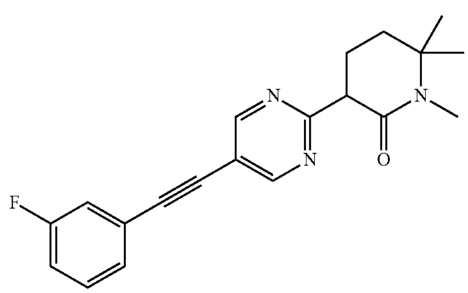 [SMILES: CN1C(=O)C(c2ncc(C#Cc3cccc(F)c3)cn2)CCC1(C)C] | (RS)-3-(5-((3-fluorophenyl)ethynyl)pyrimidin-2-yl)-1,6,6-trimethylpiperidin-2-one | 132 | 80 |
| 18 | 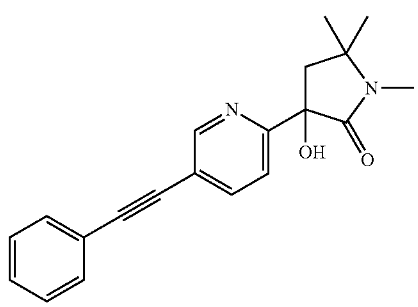 [SMILES: CN1C(=O)C(O)(c2ccc(C#Cc3ccccc3)cn2)CC1(C)C] | (RS)-3-hydroxy-1,5,5-trimethyl-3-(5-(phenylethynyl)pyridin-2-yl)pyrrolidin-2-one | 414 | 126 |

-continued

| Ex. | Structure | Name | EC$_{50}$ (nM) mGlu5 PAM | Eff. (%) |
|---|---|---|---|---|
| 19 | 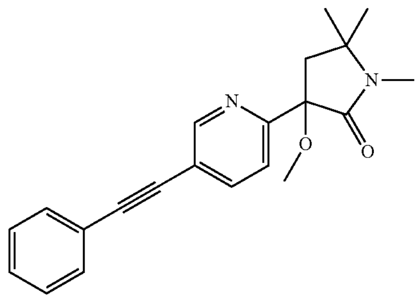 [SMILES: COC1(c2ccc(C#Cc3ccccc3)cn2)CC(C)(C)N(C)C1=O] | (RS)-3-methoxy-1,5,5-trimethyl-3-(5-(phenylethynyl)pyridin-2-yl)pyrrolidin-2-one | 96 | 108 |
| 20 | 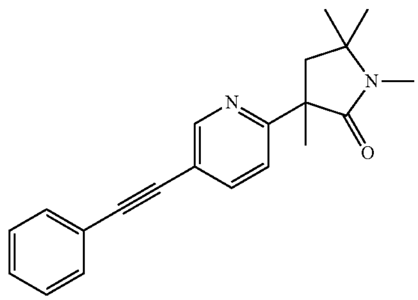 [SMILES: CN1C(=O)C(C)(c2ccc(C#Cc3ccccc3)cn2)CC1(C)C] | (RS)-1,3,5,5-tetramethyl-3-(5-(phenylethynyl)pyridin-2-yl)pyrrolidin-2-one | 90 | 109 |
| 21 | 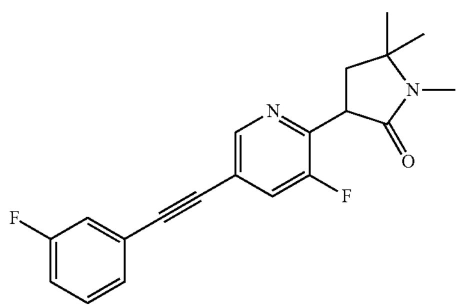 [SMILES: CN1C(=O)C(c2ncc(C#Cc3cccc(F)c3)cc2F)CC1(C)C] | (RS)-3-(3-fluoro-5-((3-fluorophenyl)ethynyl)pyridin-2-yl)-1,5,5-trimethylpyrrolidin-2-one | 188 | 91 |
| 22 | 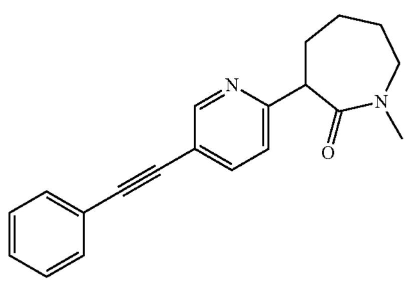 [SMILES: CN1CCCCC(c2ccc(C#Cc3ccccc3)cn2)C1=O] | (RS)-1-Methyl-3-(5-phenylethynyl-pyridin-2-yl)-azepan-2-one | 59 | 59 |
| 23 | 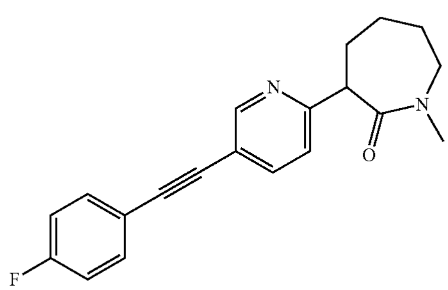 [SMILES: CN1CCCCC(c2ccc(C#Cc3ccc(F)cc3)cn2)C1=O] | (RS)-3-[5-(4-Fluoro-phenylethynyl)-pyridin-2-yl]-1-methyl-azepan-2-one | 90 | 61 |

-continued
| Ex. | Structure | Name | EC$_{50}$ (nM) mGlu5 PAM | Eff. (%) |
|---|---|---|---|---|
| 24 | 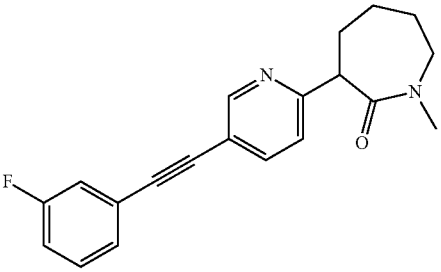 [SMILES: CN1CCCCC(c2ccc(C#Cc3cccc(F)c3)cn2)C1=O] | (RS)-3-[5-(3-Fluoro-phenylethynyl)-pyridin-2-yl]-1-methyl-azepan-2-one | 39 | 69 |
| 25 | 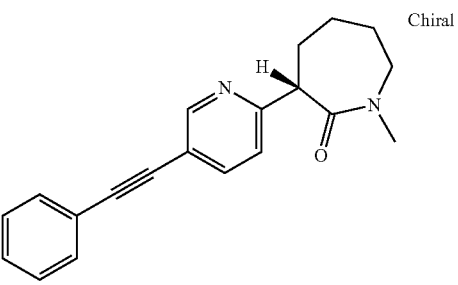 Chiral OR 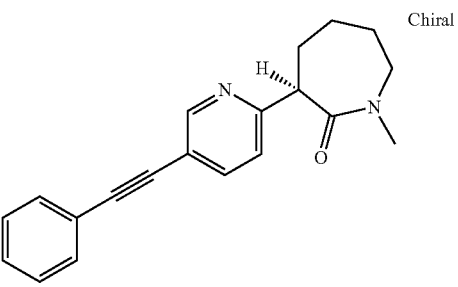 Chiral | (S or R)-1-Methyl-3-(5-phenylethynyl-pyridin-2-yl)-azepan-2-one | 35 | 70 |
| 26 | 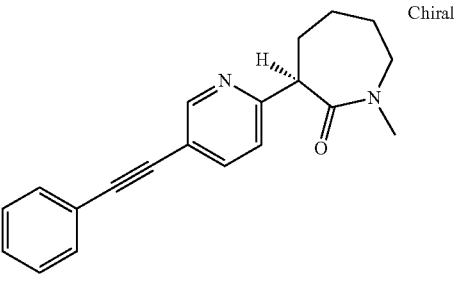 Chiral OR 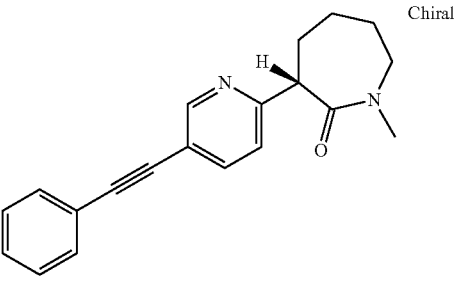 Chiral | (R or S)-1-Methyl-3-(5-phenylethynyl-pyridin-2-yl)-azepan-2-one | 265 | 69 |

-continued

| Ex. | Structure | Name | EC₅₀ (nM) mGlu5 PAM | Eff. (%) |
|---|---|---|---|---|
| 27 | 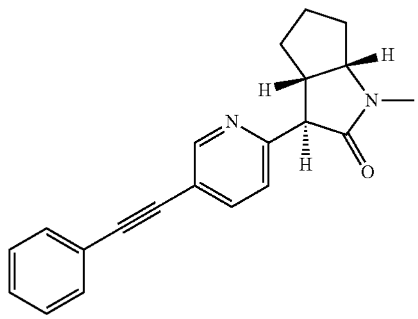 [SMILES: CN1C(=O)[C@@H](c2ccc(C#Cc3ccccc3)cn2)[C@@H]2CCC[C@@H]21] | (3RS,3aSR,6aSR)-1-Methyl-3-(5-phenylethynyl-pyridin-2-yl)-hexahydro-cyclopenta[b]pyrrol-2-one | 47 | 53 |
| 28 | Chiral ... OR ... Chiral | (3S,3aR,6aR) or (3R,3aS,6aS)-1-Methyl-3-(5-phenylethynyl-pyridin-2-yl)-hexahydro-cyclopenta[b]pyrrol-2-one | 24 | 58 |
| 29 | 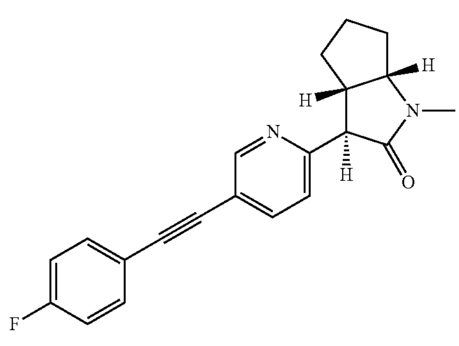 [SMILES: CN1C(=O)[C@@H](c2ccc(C#Cc3ccc(F)cc3)cn2)[C@@H]2CCC[C@@H]21] | (3RS,3aSR,6aSR)-3-[5-(4-Fluoro-phenylethynyl)-pyridin-2-yl]-1-methyl-hexahydro-cyclopenta[b]pyrrol-2-one | 78 | 53 |

| Ex. | Structure | Name | EC₅₀ (nM) mGlu5 PAM | Eff. (%) |
|---|---|---|---|---|
| 30 | 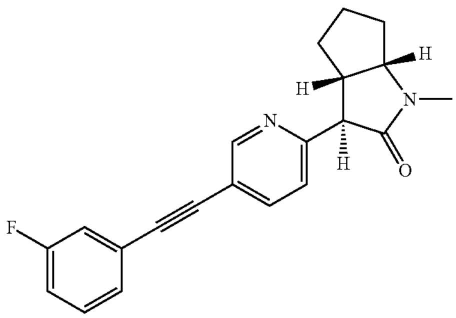 [SMILES: CN1C(=O)[C@@H](c2ccc(C#Cc3cccc(F)c3)cn2)[C@@H]2CCC[C@@H]21] | (3RS,3aSR,6aSR)-3-[5-(3-Fluoro-phenylethynyl)-pyridin-2-yl]-1-methyl-hexahydro-cyclopenta[b]pyrrol-2-one | 33 | 57 |
| 31 | Chiral / OR / Chiral | (3R,3aS,6aS) or (3S,3aR,6aR)-3-[5-(3-Fluoro-phenylethynyl)-pyridin-2-yl]-1-methyl-hexahydro-cyclopenta[b]pyrrol-2-one | 25 | 51 |
| 32 | Chiral / OR | (3S,3aR,6aR) or (3R,3aS,6aS)-3-[5-(3-Fluoro-phenylethynyl)-pyridin-2-yl]-1-methyl-hexahydro-cyclopenta[b]pyrrol-2-one | 48 | 68 |

| Ex. | Structure | Name | EC$_{50}$ (nM) mGlu5 PAM | Eff. (%) |
|---|---|---|---|---|
| | Chiral structure with 3-fluorophenylethynyl-pyridinyl group | | | |
| 33 | 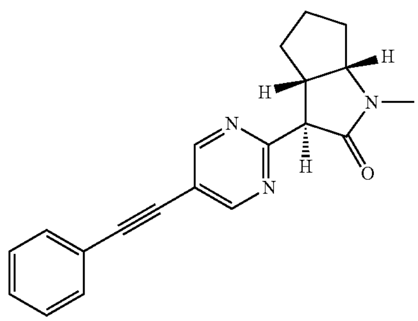 | (3RS,3aSR,6aSR)-1-Methyl-3-(5-phenylethynyl-pyrimidin-2-yl)-hexahydro-cyclopenta[b]pyrrol-2-one | 52 | 52 |
| 34 | 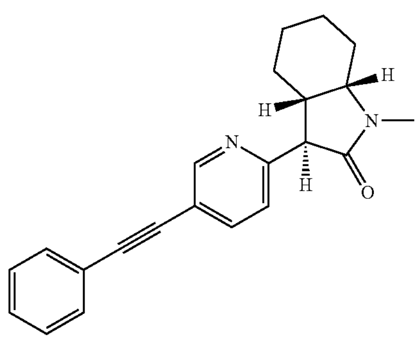 [SMILES: CN1C(=O)[C@@H](c2ccc(C#Cc3ccccc3)cn2)[C@@H]2CCCC[C@@H]21] | (3RS,6SR,7SR)-1-Methyl-3-(5-phenylethynyl-pyridin-2-yl)-octahydro-indol-2-one | 185 | 82 |
| 35 | 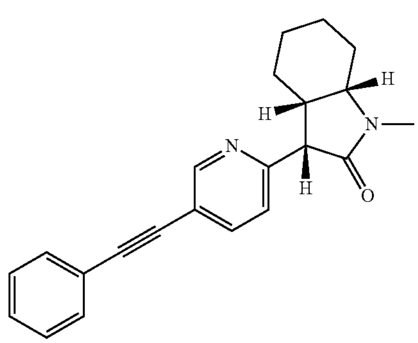 [SMILES: CN1C(=O)[C@H](c2ccc(C#Cc3ccccc3)cn2)[C@@H]2CCCC[C@@H]21] | (3SR,6SR,7SR)-1-Methyl-3-(5-phenylethynyl-pyridin-2-yl) octahydro-indol-2-one | 101 | 60 |

-continued

| Ex. | Structure | Name | EC$_{50}$ (nM) mGlu5 PAM | Eff. (%) |
|---|---|---|---|---|
| 36 | 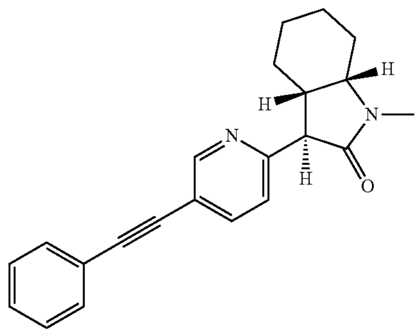 [SMILES: CN1C(=O)[C@@H](c2ccc(C#Cc3ccccc3)cn2)[C@@H]2CCCC[C@@H]21] | (3R,6S,7S)-1-Methyl-3-(5-phenylethynyl-pyridin-2-yl)-octahydro-indol-2-one | 84 | 92 |
| 37 | 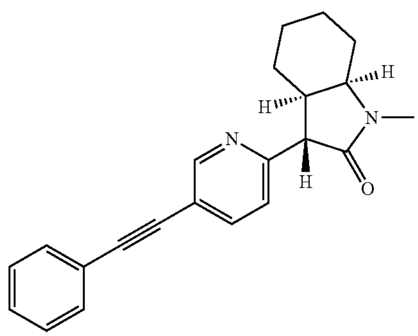 [SMILES: CN1C(=O)[C@H](c2ccc(C#Cc3ccccc3)cn2)[C@H]2CCCC[C@H]21] | (3S,6R,7R)-1-Methyl-3-(5-phenylethynyl-pyridin-2-yl)-octahydro-indol-2-one | 84 | 49 |
| 38 | 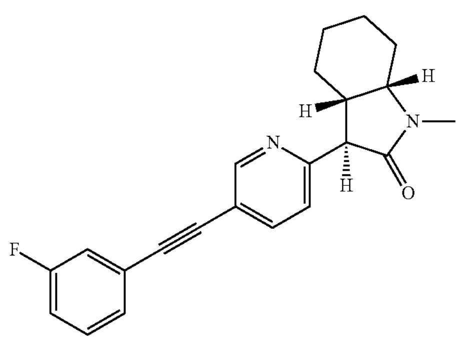 [SMILES: CN1C(=O)[C@@H](c2ccc(C#Cc3cccc(F)c3)cn2)[C@@H]2CCCC[C@@H]21] | (3RS,6SR,7SR)-3-[5-(3-Fluoro-phenylethynyl)-pyridin-2-yl]-1-methyl-octahydro-indol-2-one | 69 | 60 |
| 39 | 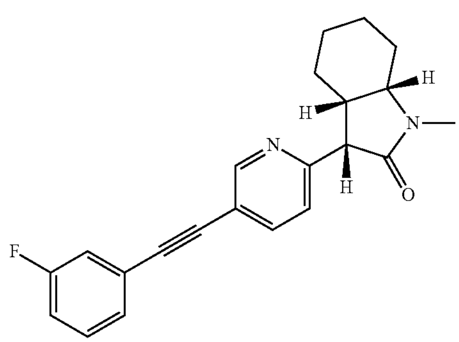 [SMILES: CN1C(=O)[C@H](c2ccc(C#Cc3cccc(F)c3)cn2)[C@@H]2CCCC[C@@H]21] | (3SR,6SR,7SR)-3-[5-(3-Fluoro-phenylethynyl)-pyridin-2-yl]-1-methyl-octahydro-indol-2-one | 141 | 61 |

-continued

| Ex. | Structure | Name | EC$_{50}$ (nM) mGlu5 PAM | Eff. (%) |
|---|---|---|---|---|
| 40 | 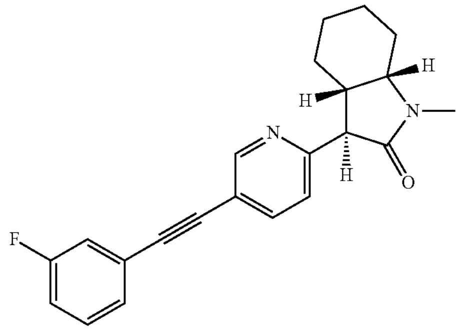 [SMILES: CN1C(=O)[C@@H](c2ccc(C#Cc3cccc(F)c3)cn2)[C@@H]2CCCC[C@@H]21] | (3R,6S,7S)-3-[5-(3-Fluoro-phenylethynyl)-pyridin-2-yl]-1-methyl-octahydro-indol-2-one | 89 | 68 |
| 41 | 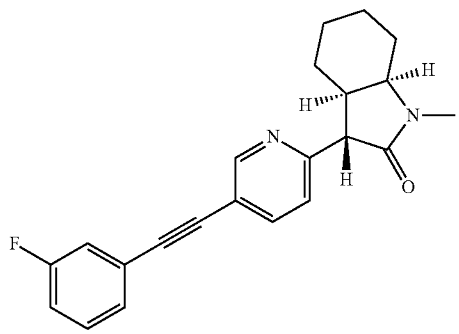 [SMILES: CN1C(=O)[C@H](c2ccc(C#Cc3cccc(F)c3)cn2)[C@H]2CCCC[C@H]21] | (3S,6R,7R)-3-[5-(3-Fluoro-phenylethynyl)-pyridin-2-yl]-1-methyl-octahydro-indol-2-one | 68 | 56 |
| 42 | 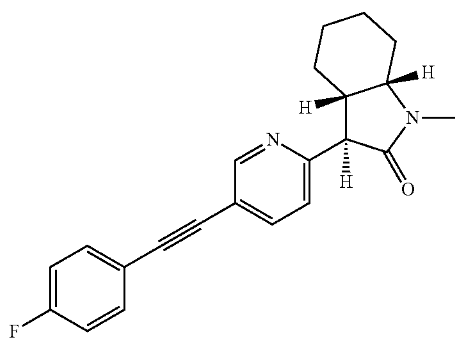 [SMILES: CN1C(=O)[C@@H](c2ccc(C#Cc3ccc(F)cc3)cn2)[C@@H]2CCCC[C@@H]21] | (3R,6S,7S)-3-[5-(4-Fluoro-phenylethynyl)-pyridin-2-yl]-1-methyl-octahydro-indol-2-one | 57 | 63 |
| 43 | 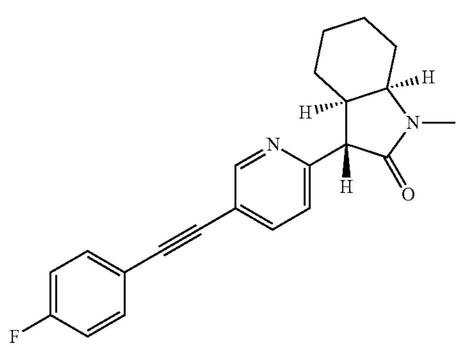 [SMILES: CN1C(=O)[C@H](c2ccc(C#Cc3ccc(F)cc3)cn2)[C@H]2CCCC[C@H]21] | (3S,6R,7R)-3-[5-(4-Fluoro-phenylethynyl)-pyridin-2-yl]-1-methyl-octahydro-indol-2-one | 146 | 53 |

-continued

| Ex. | Structure | Name | EC$_{50}$ (nM) mGlu5 PAM | Eff. (%) |
|---|---|---|---|---|
| 44 | 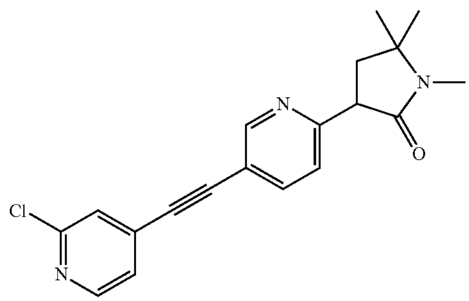 [SMILES: CN1C(=O)C(c2ccc(C#Cc3ccnc(Cl)c3)cn2)CC1(C)C] | (RS)-3-[5-(2-Chloro-pyridin-4-ylethynyl)-pyridin-2-yl]-1,5,5-trimethyl-pyrrolidin-2-one | 88 | 32 |
| 45 | Chiral ... OR ... Chiral | (S) or (R)-3-[5-(2-Chloro-pyridin-4-ylethynyl)-pyridin-2-yl]-1,5,5-trimethyl-pyrrolidin-2-one | 65 | 36 |
| 46 | Chiral ... OR | (R) or (S)-3-[5-(2-Chloro-pyridin-4-ylethynyl)-pyridin-2-yl]-1,5,5-trimethyl-pyrrolidin-2-one | 103 | 40 |

| Ex. | Structure | Name | EC₅₀ (nM) mGlu5 PAM | Eff. (%) |
|---|---|---|---|---|

The compounds of formula (I) and pharmaceutically acceptable salts thereof can be used as therapeutics, e.g. in the form of pharmaceutical compositions. The pharmaceutical compositions can be administered orally, e.g. in the form of tablets, coated tablets, drages, hard and soft gelatin capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, drages and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (1), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, the present invention provides pharmaceutical compositions containing a compound of formula (I) or pharmaceutically acceptable salts thereof and a therapeutically inert excipient. The invention also provides a process for the production of such pharmaceutical compositions which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the invention also provides methods for the treatment of the above-recited diseases by administering compounds of formula (I)

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of pharmaceutical compositions comprising compounds of the invention:

Example A

Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example 1

(RS)-1,5,5-Trimethyl-3-(5-(phenylethynyl)pyridin-2-yl)pyrrolidin-2-one

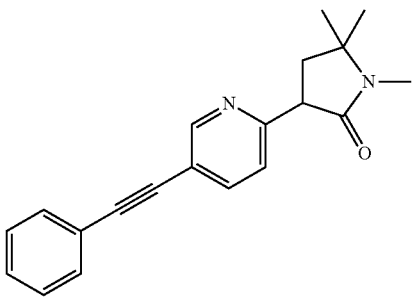 [SMILES: CN1C(=O)C(c2ccc(C#Cc3ccccc3)cn2)CC1(C)C]

Step 1: (RS)-3-(5-Iodo-pyridin-2-yl)-1,5,5-trimethyl-pyrrolidine-2-one

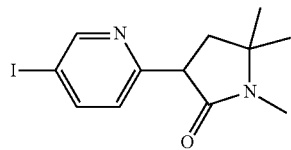 [SMILES: CN1C(=O)C(c2ccc(I)cn2)CC1(C)C]

A solution of 2-fluoro-5-iodopyridine (260 mg, 1.17 mmol) and 1,5,5-trimethyl-pyrrolidin-2-one (148 mg, 1.17 mmol) in 6 ml of dry toluene was purged with Argon and cooled to −4° C. A 1M solution of sodium hexamethyldisilylamide (NaHMDS) in toluene (2.33 ml, 2.33 mmol) was added dropwise maintaining the temperature below 0° C. The red solution was stirred for 2 h at 0° C., quenched by addition of 5 ml of saturated ammonium chloride solution. After extraction with ethyl acetate/water, drying over sodium sulfate and concentration; the residue (400 mg) was taken up in ethyl acetate, adsorbed onto 5 g of silicagel which was loaded onto a 20 g prepacked flash chromato-graphy column. After elution with a 0% to 75% ethyl acetate in heptane gradient, the fractions containing the desired product were collected to yield 145 mg (38%) of the title compound as a yellow viscous oil, MS: m/e=331.0 (M+H$^+$).

Step 2: (RS)-1,5,5-Trimethyl-3-(5-(phenylethynyl)pyridin-2-yl)pyrrolidin-2-one A solution of (RS)-3-(5-iodopyridin-2-yl)-1,5,5-trimethylpyrrolidin-2-one (140 mg, 0.42 mmol), ethynylbenzene (65.0 mg, 69.9 µl, 0.64 mmol), triethylamine (129 mg, 177 µl, 1.27 mmol), bis(triphenylphosphine)palladium (II) chloride (17.9 mg, 25.4 µmol) and triphenylphosphine (3.34 mg, 12.7 µmol) in 4 ml of THF was purged with argon. Then copper (I) iodide (2.42 mg, 12.7 µmol) was added and the reaction was heated for 3 h at 60° C. After extraction with ethyl acetate/water, drying over sodium sulfate and concentration; the residue was taken up in ethyl acetate, adsorbed onto 3 g of silicagel which was loaded onto a 20 g prepacked flash chromato-graphy column. After elution with a 0% to 65% ethyl acetate in heptane gradient, the fractions containing the desired product were collected to yield 103 mg (72%) of the title compound as an amorphous yellow solid, MS: m/e=305.2 (M+H$^+$).

Example 2

(RS)-1,5,5-Trimethyl-3-(5-(pyridin-3-ylethynyl)pyridin-2-yl)pyrrolidin-2-one

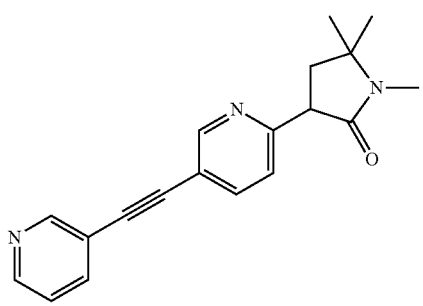 [SMILES: CN1C(=O)C(c2ccc(C#Cc3cccnc3)cn2)CC1(C)C]

The title compound was obtained as an amorphous yellow solid, MS: m/e=306.2 (M+H$^+$), using chemistry similar to that described in Example 1, step 2 from (RS)-3-(5-iodopyridin-2-yl)-1,5,5-trimethylpyrrolidin-2-one (Example 1, step 1) and 3-ethynyl-pyridine.

Example 3

(RS)-3-(5-((3-Chlorpheny)ethynyl)pyridin-2-yl)-1,5,5-trimethylpyrrolidin-2-one

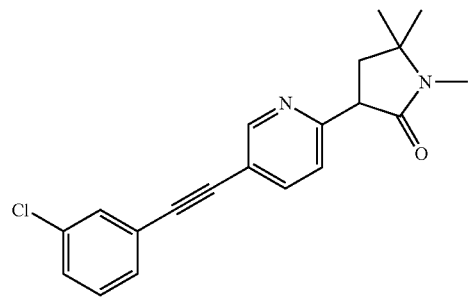

The title compound was obtained as a yellow viscous oil, MS: m/e=339.1, 341.1 (M+H$^+$), using chemistry similar to that described in Example 1, step 2 from (RS)-3-(5-iodopyridin-2-yl)-1,5,5-trimethylpyrrolidin-2-one (Example 1, step 1) and 3-ethynyl-3-chloro-benzene.

Example 4

(RS)-3-(5-((3-Fluorophenyl)ethynyl)pyridin-2-yl)-1,5,5-trimethylpyrrolidin-2-one

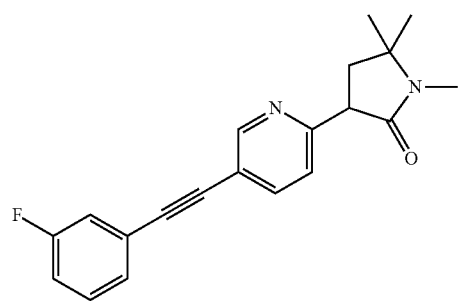 [SMILES: CN1C(=O)C(c2ccc(C#Cc3cccc(F)c3)cn2)CC1(C)C]

The title compound was obtained as a yellow viscous oil, MS: m/e=323.3 (M+H$^+$), using chemistry similar to that described in Example 1, step 2 from (RS)-3-(5-iodopyridin- 2-yl)-1,5,5-trimethylpyrrolidin-2-one (Example 1, step 1) and 1-ethynyl-3-fluoro-benzene.

Example 5

(RS)-Benzyl 1,5,5-trimethyl-2-oxo-3-(5-(phenylethynyl)pyrimidin-2-yl)pyrrolidine-3-carboxylate

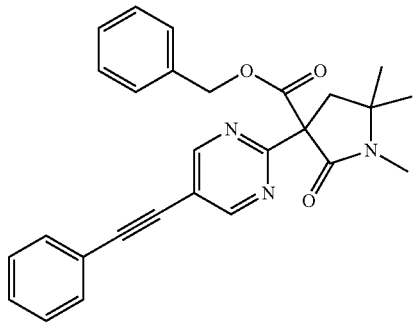 [SMILES: CN1C(=O)C(C(=O)OCc2ccccc2)(c2ncc(C#Cc3ccccc3)cn2)CC1(C)C]

Step 1: (RS)-1,5,5-Trimethyl-2-oxo-pyrrolidine-3-carboxylic acid benzyl ester

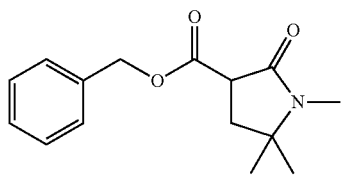 [SMILES: CN1C(=O)C(C(=O)OCc2ccccc2)CC1(C)C]

In a flame-dried 50 ml three necked flask under argon atmosphere were dissolved 1.27 g (10.0 mmol) of 5,5-dimethylpyrrolidin-2-one in 10 ml of dry THF. After cooling to −75° C., a 2 M solution of lithium diisopropylamide in THF (10.5 ml, 10.5 mmol) was added dropwise maintaining the temperature below −73° C. The solution was stirred for 1 h at −75° C. Then a solution of dibenzyl carbonate (2.72 g, 11.0 mmol) in 5 ml of THF was added dropwise at −75° C., allowed to warm up to r.t. and stirred for 1 h. The reaction was quenched by addition of 5 ml of saturated ammonium chloride solution. After extraction with ethyl acetate/water, drying over sodium sulfate and concentration; the residue was loaded onto a 50 g prepacked flash chromatography column. After elution with a 10% to 70% ethyl acetate in heptane gradient, the fractions containing the desired product were collected to yield 1.07 g (41%) of the title compound as a light yellow oil, MS: m/e=262.2 (M+H$^+$).

Step 2: (RS)-Benzyl 1,5,5-trimethyl-2-oxo-3-(5-(phenylethynyl)pyrimidin-2yl)-pyrrolidine-3-carboxylate A solution of (RS)-benzyl 1,5,5-trimethyl-2-oxopyrrolidine-3-carboxylate (206 mg, 787 μmol) in 4 ml of dry DMF was purged with argon and cooled to 0° C. Then a 60% suspension of sodium hydride (31.5 mg, 0.79 mmol) was added and the mixture was stirred for 40 min at room temperature whereby a white suspension was formed. Then 2-chloro-5-(phenylethynyl)pyrimidine (CAS: [1051388-40-9]) (130 mg, 606 μmol) was added, the mixture was stirred for 30 min at 80° C., and then quenched by addition of 1 ml of saturated ammonium chloride solution. After extraction with ethyl acetate/water, drying over sodium sulfate and concentration; the residue (440 mg, yellow oil) was taken up in ethyl acetate, adsorbed onto 3 g of silicagel and loaded onto a 20 g prepacked flash chromatography column. After elution with a 10% to 60% ethyl acetate in heptane gradient, the fractions containing the desired product were collected to yield 212 mg (80%) of the title compound as a light yellow waxy solid, MS: m/e=440.3 (M+H$^+$).

Example 6

(RS)-1,5,5-Trimethyl-3-(5-(phenylethynyl)pyrimidin-2-yl)pyrrolidin-2-one

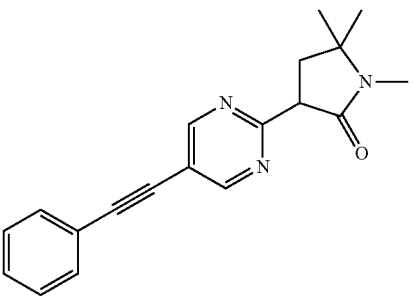 [SMILES: CN1C(=O)C(c2ncc(C#Cc3ccccc3)cn2)CC1(C)C]

To a solution of (RS)-benzyl 1,5,5-trimethyl-2-oxo-3-(5-(phenylethynyl)pyrimidin-2-yl)pyrrolidine-3-carboxylate (Example 5, step 2) (205 mg, 0.47 μmol) in 3 ml of ethanol was added 1N sodium hydroxide solution (933 μl, 0.94 mmol). After stirring for 1.5 h at room temperature, the pH was neutralized by addition of 1N HCl, and the solvent was evaporated in vaccuo. The residue (165 mg, yellow oil) was loaded onto a 20 g prepacked flash chromatography column. After elution with a 15% to 100% ethyl acetate in heptane gradient, the fractions containing the desired product were collected to yield 94 mg (66%) of the title compound as a light yellow crystalline solid, MS: m/e=306.2 (M+H$^+$).

Example 7

(RS)-3-(5-((3-Fluorophenyl)ethynyl)pyrimidin-2-yl)-1,5,5-trimethylpyrrolidin-2-one

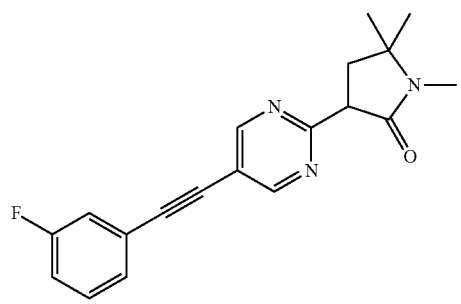

Step 1: (RS)-3-(5-Bromo-pyrimidin-2-yl)-1,5,5-trimethyl-2-oxo-pyrrolidine-3-carboxylic acid benzyl ester

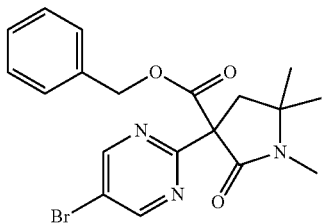 [SMILES: CN1C(=O)C(C(=O)OCc2ccccc2)(c2ncc(Br)cn2)CC1(C)C]

The title compound was obtained as a colorless viscous oil, MS: m/e=420.1, 418.2 (M+H$^+$), using chemistry similar to that described in Example 5, step 2 from (RS)-benzyl 1,5,5-trimethyl-2-oxopyrrolidine-3-carboxylate (Example 5, step 1) and 5-bromo-2-chloropyrimidine Step 2: (RS)-3-(5-Bromo-pyrimidin-2-yl)-1,5,5-trimethyl-pyrrolidin-2-one

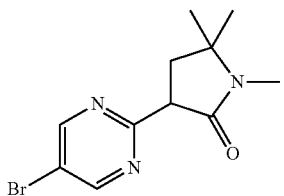 [SMILES: CN1C(=O)C(c2ncc(Br)cn2)CC1(C)C]

The title compound was obtained as a crystalline white solid, MS: m/e=284.0, 286.0 (M+H$^+$), using chemistry similar to that described in Example 6 from (RS)-3-(5-bromo-pyrimidin-2-yl)-1,5,5-trimethyl-2-oxo-pyrrolidine-3-carboxylic acid benzyl ester.

Step 3: (RS)-3-(5-((3-Fluoropheny)ethynyl)pyrimidin-2-yl)-1,5,5-trimethylpyrrolidin-2-one The title compound was obtained as a crystalline white solid, MS: m/e=324.2 (M+H$^+$), using chemistry similar to that described in Example 1, step 2 from (RS)-3-(5-iodopyridin-2-yl)-1,5,5-trimethylpyrrolidin-2-one and 1-ethynyl-3-fluoro-benzene.

Example 8

(RS)-3-(5-((4-Fluorophenyl)ethynyl)pyrimidin-2-yl)-1,5,5-trimethylpyrrolidin-2-one

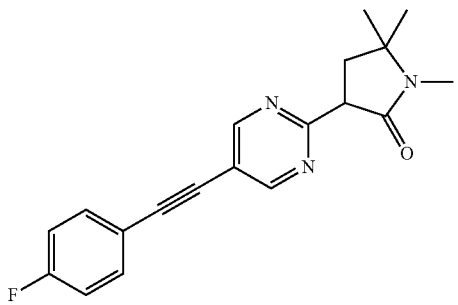 [SMILES: CN1C(=O)C(c2ncc(C#Cc3ccc(F)cc3)cn2)CC1(C)C]

Step 1: 2-Chloro-5-(4-fluoro-phenylethynyl)-pyrimidine

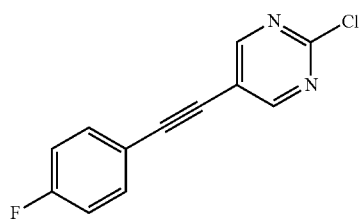 [SMILES: Fc1ccc(C#Cc2cnc(Cl)nc2)cc1]

A solution of 2-chloro-5-iodopyrimidine (600 mg, 2.5 mmol), 1-ethynyl-4-fluorobenzene (330 mg, 2.75 mmol), triethylamine (556 mg, 761 µl, 5.49 mmol), and bis(triphenylphosphine)palladium (II) chloride (175 mg, 250 µmol) in 7 ml of THF was purged with argon. Then copper (I) iodide (23.8 mg, 125 µmol) was added and the reaction was heated for 2 h at room temperature. The dark solution was filtered and the solids were washed with THF. The residue was taken up in ethyl acetate, adsorbed onto 3 g of silicagel which was loaded onto a 50 g prepacked flash chromatography column. After elution with a 0% to 20% ethyl acetate in heptane gradient, the fractions containing the desired product were collected to yield 505 mg (87%) of the title compound as an crystalline light yellow solid, MS: m/e=233.1, 235.1 (M+H$^+$).

Step 2: 3-[5-(4-Fluoro-phenylethynyl)-pyrimidin-2-yl]-1,5,5-trimethyl-2-oxo-pyrrolidine-3-carboxylic acid benzyl ester

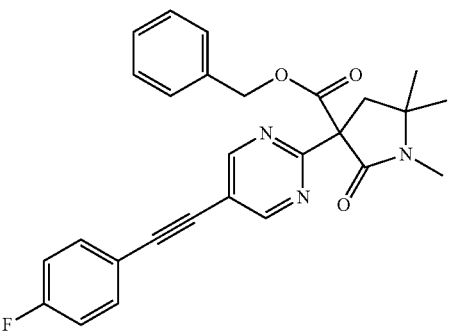 [SMILES: CN1C(=O)C(C(=O)OCc2ccccc2)(c2ncc(C#Cc3ccc(F)cc3)cn2)CC1(C)C]

The title compound was obtained as a light yellow viscous oil, MS: m/e=458.3 (M+H$^+$), using chemistry similar to that described in Example 5, step 2 from (RS)-1,5,5-trimethyl-2-oxo-pyrrolidine-3-carboxylic acid benzyl ester (Example 5, step 1) and 2-chloro-5-(4-fluoro-phenylethynyl)-pyrimidine.

Step 3: (RS)-3-(5((4-Fluorophenyl)ethynyl)pyrimidin-2-yl)-1,5,5-trimethylpyrrolidin-2-one The title compound was obtained as a white waxy solid, MS: m/e=324.2 (M+H$^+$), using chemistry similar to that described in Example 6 from 3-[5-(4-fluoro-phenylethynyl)-pyrimidin-2-yl]-1,5,5-trimethyl-2-oxo-pyrrolidine-3-carboxylic acid benzyl ester.

Example 9

(RS)-3-(6-((3-Fluorophenyl)ethynyl)pyridazin-3-yl)-1,5,5-trimethylpyrrolidin-2-one

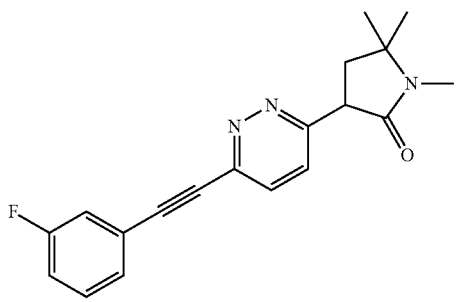 [SMILES: CN1C(=O)C(c2ccc(C#Cc3cccc(F)c3)nn2)CC1(C)C]

Step 1: 3-Chloro-6-(3-fluoro-phenylethynyl)-pyridazine

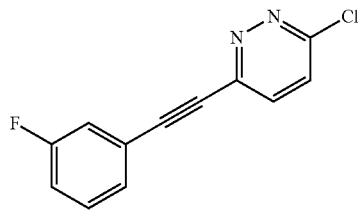 [SMILES: Fc1cccc(C#Cc2ccc(Cl)nn2)c1]

The title compound was obtained as a crystalline light yellow solid, MS: m/e=233.1, 235.0 (M+H$^+$), using chemistry similar to that described in Example 8, step 1 from 3-chloro-6-iodopyridazine and 1-ethynyl-3-fluorobenzene.

Step 2: (RS)-3-[6-(3-Fluoro-phenylethynyl)-pyridazin-3-yl]-1,5,5-trimethyl-2-oxo-pyrrolidine-3-carboxylic acid benzyl ester

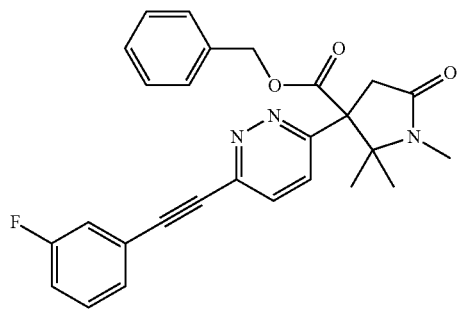 [SMILES: CN1C(=O)CC(C(=O)OCc2ccccc2)(c2ccc(C#Cc3cccc(F)c3)nn2)C1(C)C]

The title compound was obtained as a yellow gum, MS: m/e=458.3 (M+H$^+$), using chemistry similar to that described in Example 5, step 2 from (RS)-1,5,5-trimethyl-2-oxo-pyrrolidine-3-carboxylic acid benzyl ester (Example 5, step 1) and 3-chloro-6-(3-fluoro-phenylethynyl)-pyridazine.

Step 3: (RS)-3-(6-((3-fluorophenyl)ethynyl)pyridazin-3-yl)-1,5,5-trimethylpyrrolidin-2-one The title compound was obtained as a colorless viscous oil, MS: m/e=324.2 (M+H$^+$), using chemistry similar to that described in Example 6 from (RS)-3-[6-(3-fluoro-phenylethynyl)-pyridazin-3-yl]-1,5,5-trimethyl-2-oxo-pyrrolidine-3-carboxylic acid benzyl ester.

Example 10

(RS)-3-(6((4-Fluorophenyl)ethynyl)pyridazin-3-yl)-1,5,5-trimethylpyrrolidin-2-one

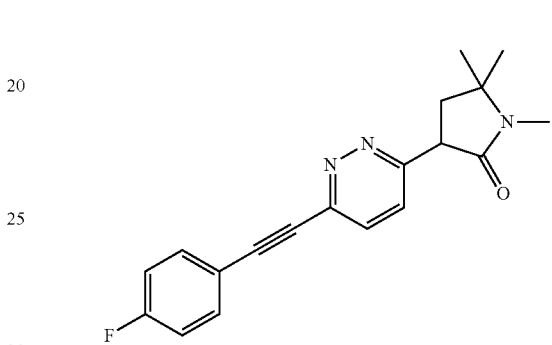

Step 1: 3-Chloro-6-(4-fluoro-phenylethynyl)-pyridazine

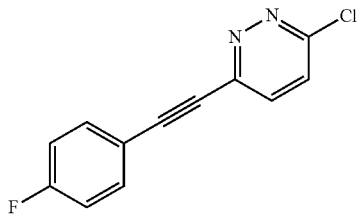 [SMILES: Fc1ccc(C#Cc2ccc(Cl)nn2)cc1]

The title compound was obtained as a crystalline light yellow solid, MS: m/e=233.1, 235.1 (M+H$^+$), using chemistry similar to that described in Example 8, step 1 from 3-chloro-6-iodopyridazine and 1-ethynyl-4-fluorobenzene.

Step 2: (RS)-3-[6-(3-Fluoro-phenylethynyl)-pyridazin-3-yl]-1,5,5-trimethyl-2-oxo-pyrrolidine-3-carboxylic acid benzyl ester

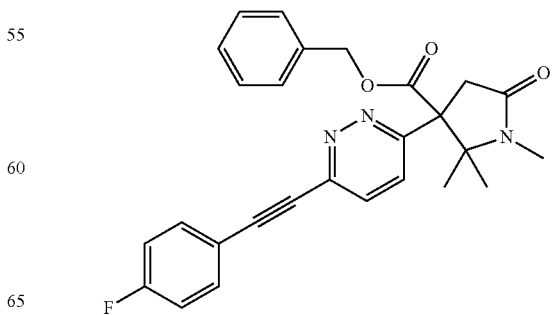

The title compound was obtained as a yellow viscous oil, MS: m/e=458.3 (M+H⁺), using chemistry similar to that described in Example 5, step 2 from (RS)-1,5,5-trimethyl-2-oxo-pyrrolidine-3-carboxylic acid benzyl ester (example 5, step 1) and 3-chloro-6-(4-fluoro-phenylethynyl)-pyridazine.

Step 3: (RS)-3-(6-((3-Fluorophenyl)ethynyl)pyridazin-3-yl)-1,5,5-trimethylpyrrolidin-2-one The title compound was obtained as a colorless viscous oil, MS: m/e=324.2 (M+H⁺), using chemistry similar to that described in Example 6 from (RS)-3-[6-(4-fluoro-phenylethynyl)-pyridazin-3-yl]-1,5,5-trimethyl-2-oxo-pyrrolidine-3-carboxylic acid benzyl ester.

Example 11

(S)-3-(6-(Phenylethynyl)pyridazin-3-yl)-1,5,5-trimethylpyrrolidin-2-one

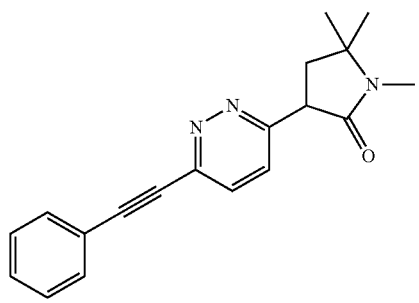 [SMILES: CN1C(=O)C(c2ccc(C#Cc3ccccc3)nn2)CC1(C)C]

Step 1: 3-Chloro-6-(phenylethynyl)-pyridazine

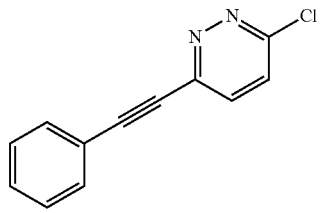 [SMILES: Clc1ccc(C#Cc2ccccc2)nn1]

The title compound was obtained as a crystalline light yellow solid, MS: m/e=215.2, 217.2 (M+H⁺), using chemistry similar to that described in Example 8, step 1 from 3-chloro-6-iodopyridazine and 1-ethynyl-benzene.

Step 2: (RS)-3-[6-(Phenylethynyl)-pyridazin-3-yl]-1,5,5-trimethyl-2-oxo-pyrrolidine-3-carboxylic acid benzyl ester

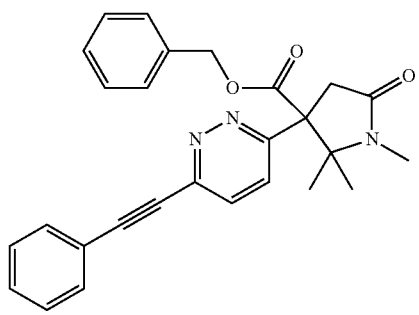 [SMILES: CN1C(=O)CC(C(=O)OCc2ccccc2)(c2ccc(C#Cc3ccccc3)nn2)C1(C)C]

The title compound was obtained as a light yellow oil, MS: m/e=440.2 (M+H⁺), using chemistry similar to that described in Example 5, step 2 from (RS)-1,5,5-trimethyl-2-oxo-pyrrolidine-3-carboxylic acid benzyl ester (Example 5, step 1) and 3-chloro-6-(phenylethynyl)-pyridazine.

Step 3: (RS)-3-(6-(Phenylethynyl)pyridazin-3-yl)-1,5,5-trimethylpyrrolidin-2-one The title compound was obtained as a yellow waxy solid, MS: m/e=3063 (M+H⁺), using chemistry similar to that described in Example 6 from (RS)-3-[6-(phenylethynyl)-pyridazin-3-yl]-1,5,5-trimethyl-2-oxo-pyrrolidine-3-carboxylic acid benzyl ester.

Example 12

(RS)-1,6,6-Trimethyl-3-(5-(phenylethynyl)pyridin-2-yl)piperidin-2-one

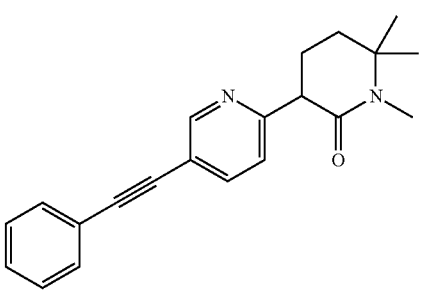 [SMILES: CN1C(=O)C(c2ccc(C#Cc3ccccc3)cn2)CCC1(C)C]

Step 1: 3 to 1 Mixture of 6,6-dimethyl-piperidin-2-one and 3,3-dimethyl-piperidin-2-one

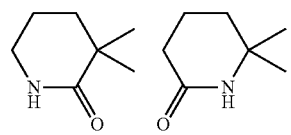

To 9.97 g (88.9 mmol) of 2,2,-dimethylcyclopentanone were added 70 ml of 98% formic acid with stirring. To this clear solution was added 15.1 g (133 mmol) of hydroxylamine-O-sulfonic acid in portions, maintaining the temperature between 15-20° C. using an ice-bath. After stirring for 5 min the white suspension became a clear solution. The mixture was then refluxed for 4 h (100° C.) and allowed to cool overnight. The resulting yellow solution was concentrated in vaccuo. The light orange resinous residue was taken up in 30 ml of water, 40 ml of 1N sodium hydroxide solution and 100 ml of chloroform and vigourously stirred until dissolution was complete. The pH of the aqueous phase was adjusted to 8 by addition of 25% NaOH solution. The organic phase was separated. The aqueous phase was extracted five times with 30 ml of chloroform. The combined organic phases were washed with 10 ml of water. The combined organic phases were concentrated in vaccuo to yield 9.9 g of a light orange semi-solid which was purified by chromatography over silicagel (ethyl acetate/methanol 9:1). Fractions containing the two isomers were collected to yield 4.72 g (41.8%) of a white solid which was directly used in the next step.

Step 2: 1,6,6-Trimethyl-piperidin-2-one

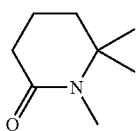

To a solution of a 3 to 1 mixture of 3,3-dimethylpiperidin-2-one and 6,6-dimethylpiperidine-2-one (4.72 g, 37.1 mmol) in 60 ml of THF was added 60% sodium hydride suspension (1.93g, 48.2 mmol). The grey reaction mixture was stirred at room temperature for 30 minutes. Then methyl iodide (3.02 ml, 48.2 mmol) was added and the reaction mixture was stirred at room temperature overnight. The reaction mixture was quenched with water, and worked up with ethyl acetate/water. The orange oil was chromatographed over a prepacked 70 g silica column After elution with a 50% to 100% ethyl acetate in heptane gradient, the fractions containing the desired product were collected to yield 2.46 g (47%) of the title compound as a light yellow solid; and 0.91 g (17%) of isomeric 1,3,3-trimethyl-piperidin-2-one as a yellow oil.

Step 2: (RS)-5-Iodo-1',6',6'-trimethyl-3',4',5',6'-tetrahydro-1'H-[2,3']bipyridinyl-2'-one

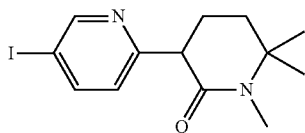 [SMILES: CN1C(=O)C(c2ccc(I)cn2)CCC1(C)C]

The title compound was obtained as a colorless viscous oil, MS: m/e=345.1 (M+H$^+$), using chemistry similar to that described in Example 1, step 1 from 1,6,6-trimethyl-piperidin-2-one and 2-fluoro-5-iodopyridine.

Step 3: 5 (RS)-1,6,6-Trimethyl-3-(5-(phenylethynyl)pyridin-2-yl)piperidin-2-one The title compound was obtained as a light yellow viscous oil, MS: m/e=319.2 (M+H$^+$), using chemistry similar to that described in Example 1, step 2 from (RS)-5-iodo-1',6',6'-trimethyl-3',4',5',6'-tetrahydro-1'H-[2,3']bipyridinyl-2'-one and 3-ethynyl-pyridine.

Example 13

(RS)-3-(5-((3-Fluorophenyl)ethynyl)pyridin-2-yl)-1,6,6-trimethylpiperidin-2-one

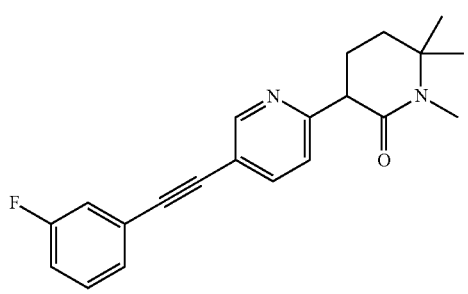

The title compound was obtained as a light yellow viscous oil, MS: m/e=337.2 (M+H$^+$) using chemistry similar to that described in Example 1, step 2 from (RS)-5-iodo-1',6',6'-trimethyl-3',4',5',6'-tetrahydro-1'H-[2,3']bipyridinyl-2'-one and 1-ethynyl-3-fluoro-benzene.

Example 14

(RS)-3-(5-((4-Fluorophenyl)ethynyl)pyridin-2-yl)-1,6,6-trimethylpiperidin-2-one

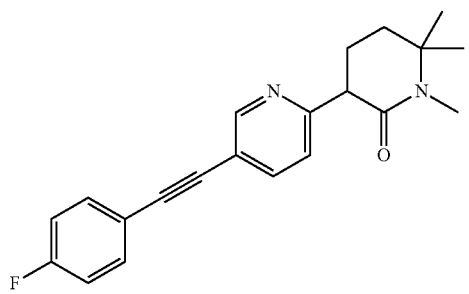

The title compound was obtained as a light yellow waxy solid, MS: m/e=337.2 (M+H$^+$), using chemistry similar to that described in Example 1, step 2 from (RS)-5-iodo-1',6',6'-trimethyl-3',4',5',6'-tetrahydro-1'H-[2,3']bipyridinyl-2'-one and 1-ethynyl-4-fluoro-benzene.

Example 15

(RS)-1,6,6-Trimethyl-3-(5-(phenylethynyl)pyrimidin-2-yl)piperidin-2-one

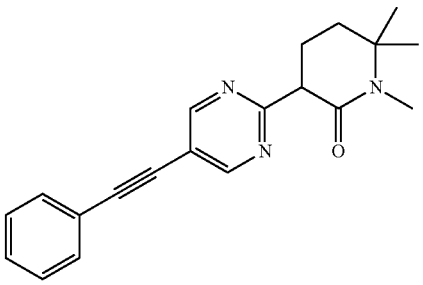 [SMILES: CN1C(=O)C(c2ncc(C#Cc3ccccc3)cn2)CCC1(C)C]

Step 1: (RS)-1,6,6-Trimethyl-2-oxo-piperidine-3-carboxylic acid benzyl ester

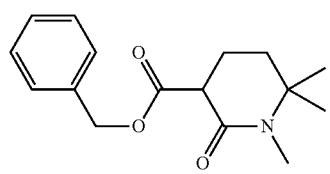 [SMILES: CN1C(=O)C(C(=O)OCc2ccccc2)CCC1(C)C]

The title compound was obtained as a light yellow oil, using chemistry similar to that described in Example 5, step 1 from 1,6,6-trimethyl-piperidin-2-one and dibenzyl carbonate.

Step 2: (RS)-1,6,6-Trimethyl-2-oxo-3-(5-phenylethynyl-pyrimidin-2-yl)-piperidine-3-carboxylic acid benzyl ester

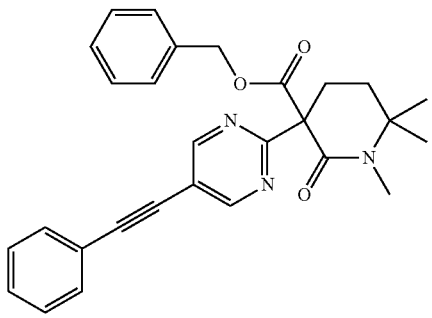 [SMILES: CN1C(=O)C(C(=O)OCc2ccccc2)(c2ncc(C#Cc3ccccc3)cn2)CCC1(C)C]

The title compound was obtained as a yellow oil, using chemistry similar to that described in Example 5, step 2 from (RS)-1,6,6-trimethyl-2-oxo-piperidine-3-carboxylic acid benzyl ester and 2-chloro-5-(phenylethynyl)pyrimidine (CAS: [1051388-40-9]).

Step 3: (RS)-1.6,6-Trimethyl-3-(5-(phenylethynyl pyrimidin-2-yl)piperidin-2-one

The title compound was obtained as a light yellow solid, MS: m/e=320.2 (M+H$^+$), using chemistry similar to that described in Example 6 from (RS)-1,6,6-trimethyl-2-oxo-3-(5-phenylethynyl-pyrimidin-2-yl)-piperidine-3-carboxylic acid benzyl ester.

Example 16

(RS)-3-(5-((4-Fluorophenyl)ethynyl)pyrimidin-2-yl)-1,6,6-trimethylpiperidin-2-one

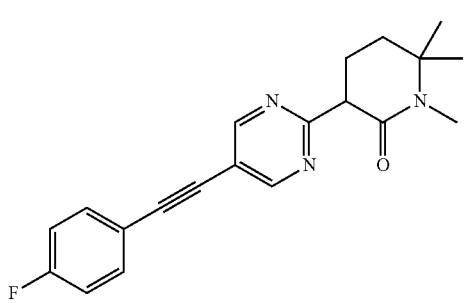 [SMILES: CN1C(=O)C(c2ncc(C#Cc3ccc(F)cc3)cn2)CCC1(C)C]

Step 1: (RS)-1,6,6-Trimethyl-2-oxo-3-(5-((4-fluorophenyl)ethynyl)-pyrimidin-2-yl)-piperidine-3-carboxylic acid benzyl ester

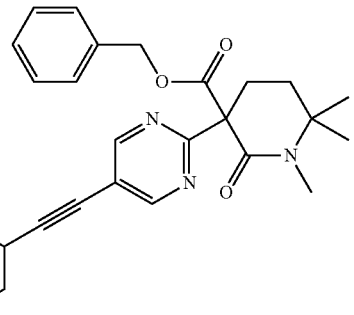

The title compound was obtained as an orange oil, using chemistry similar to that described in Example 5, step 2 from (RS)-1,6,6-trimethyl-2-oxo-piperidine-3-carboxylic acid benzyl ester and 2-chloro-5-(4-fluoro-phenylethynyl)-pyrimidine (Example 8, step 1).

Step 2: (RS)-3-(5-((4-Fluorophenyl)ethynyl)pyrimidin-2-yl)-1,6k-trimethylpiperidin-2-one The title compound was obtained as an off-white solid, MS: m/e=338.2 (M+H$^+$), using chemistry similar to that described in Example 6 from (RS)-1,6,6-trimethyl-2-oxo-3-(5-((4-fluorophenyl)ethynyl)-pyrimidin-2-yl)-piperidine-3-carboxylic acid benzyl ester.

Example 17

(RS)-3-(5((3-Fluorophenyl)ethynyl)pyrimidin-2-yl)-1,6,6-trimethylpiperidin-2-one

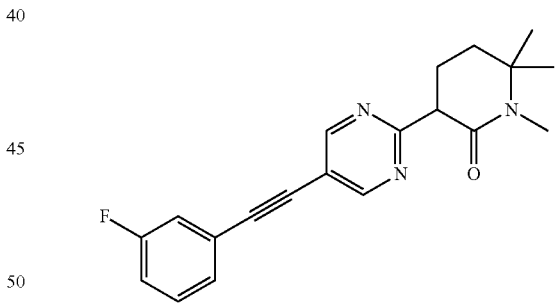

Step 1:
2-Chloro-5-(3-fluoro-phenylethynyl)-pyrimidine

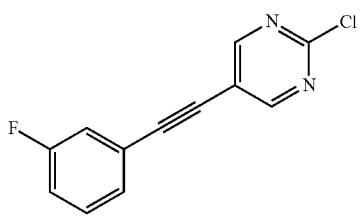 [SMILES: Fc1cccc(C#Cc2cnc(Cl)nc2)c1]

The title compound was obtained as a yellow solid, MS: m/e=233.0, 234.9 (M+H⁺), using chemistry similar to that described in Example 8, step 1 from 2-chloro-5-iodopyrimidine and 1-ethynyl-3-fluorobenzene.

Step 2: (RS)-1,6,6-Trimethyl-2-oxo-3-(5-((3-fluorophenyl)ethynyl)-pyrimidin-2-yl)-piperidine-3-carboxylic acid benzyl ester

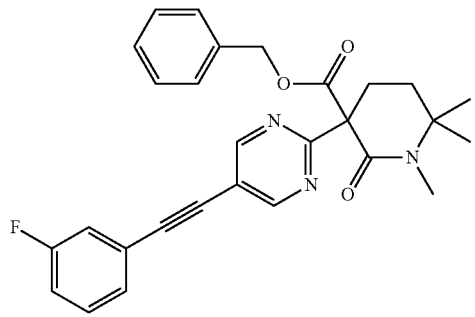 [SMILES: CN1C(=O)C(C(=O)OCc2ccccc2)(c2ncc(C#Cc3cccc(F)c3)cn2)CCC1(C)C]

The title compound was obtained as a yellow oil, using chemistry similar to that described in example 5, step 2 from (RS)-1,6,6-trimethyl-2-oxo-piperidine-3-carboxylic acid benzyl ester and 2-chloro-5-(3-fluoro-phenylethynyl)-pyrimidine (Example 8, step 1).

Step 3: (RS)-3-(5-((4-Fluorophenyl)ethynyl)pyrimidin-2-yl)-1,6,6-trimethylpiperidin-2-one The title compound was obtained as a light brown solid, MS: m/e=338.2 (M+H⁺), using chemistry similar to that described in Example 6 from (RS)-1,6,6-trimethyl-2-oxo-3-(5-((3-fluorophenyl)ethynyl)-pyrimidin-2-yl)-piperidine-3-carboxylic acid benzyl ester.

Example 18

(RS)-3-Hydroxy-1,5,5-trimethyl-3-(5-(phenylethynyl)pyridin-2-yl)pyrrolidin-2-one

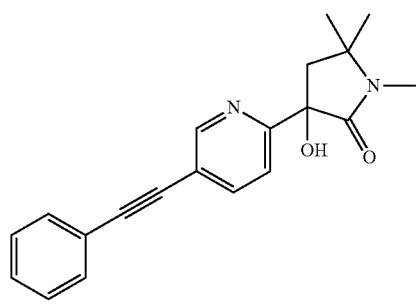 [SMILES: CN1C(=O)C(O)(c2ccc(C#Cc3ccccc3)cn2)CC1(C)C]

The title compound was obtained as byproduct in the synthesis of Example 1 as a light brown oil, MS: m/e=321.2 (M+H⁺).

Example 19

(RS)-3-Methoxy-1,5,5-trimethyl-3-(5-(phenylethynyl)pyridin-2-yl)pyrrolidin-2-one

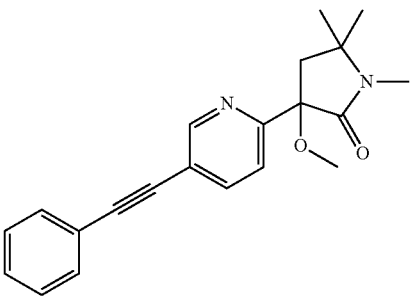 [SMILES: COC1(c2ccc(C#Cc3ccccc3)cn2)CC(C)(C)N(C)C1=O]

The title compound was obtained as a light yellow oil, MS: m/e=335.2 (M+H⁺), using chemistry similar to that described in Example 12, step 2 from (RS)-3-hydroxy-1,5,5-trimethyl-3-(5-(phenylethynyl)pyridin-2-yl)pyrrolidin-2-one (Example 18) and iodomethane.

Example 20

(RS)-1,3,5,5-Tetramethyl-3-(5-(phenylethynyl)pyridin-2-yl)pyrrolidin-2-one

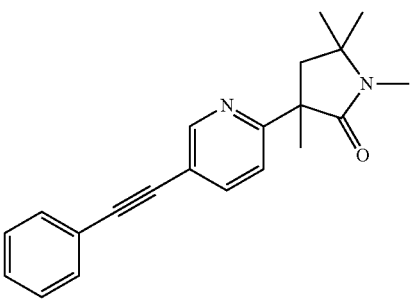 [SMILES: CN1C(=O)C(C)(c2ccc(C#Cc3ccccc3)cn2)CC1(C)C]

Step 1: (RS)-3-(5-Iodo-pyridin-2-yl)-1,3,5,5-tetramethyl-pyrrolidin-2-one

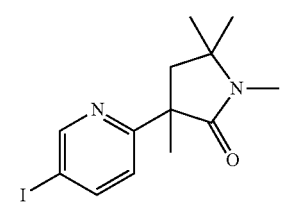 [SMILES: CN1C(=O)C(C)(c2ccc(I)cn2)CC1(C)C]

The title compound was obtained as a white solid, MS: m/e=345.0 (M+H⁺), using chemistry similar to that described in Example 12, step 2 from (RS)-3-(5-iodo-pyridin-2-yl)-1,5,5-trimethyl-pyrrolidin-2-one (Example 1, step 1) and iodomethane.

Step 2: (RS)-1,3,5,5-Tetramethyl-3-(5-(phenylethynyl)pyridin-2-yl)pyrrolidin-2-one

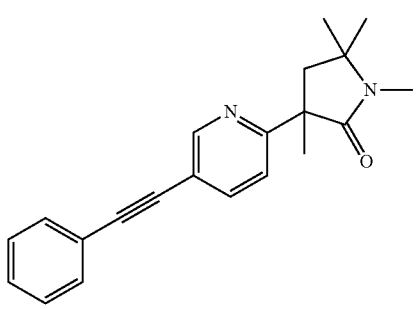 [SMILES: CN1C(=O)C(C)(c2ccc(C#Cc3ccccc3)cn2)CC1(C)C]

The title compound was obtained as a light brown oil, MS: m/e=319.1 (M+H⁺), using chemistry similar to that described in Example 1, step 2 from (RS)-3-(5-iodo-pyridin-2-yl)-1,3,5,5-tetramethyl-pyrrolidin-2-one (Example 20, step 1) and phenylacetylene.

Example 21

(RS)-3-(3-fluorophenyl)ethynyl)pyridin-2-yl)-1,5,5-trimethylpyrrolidin-2-one

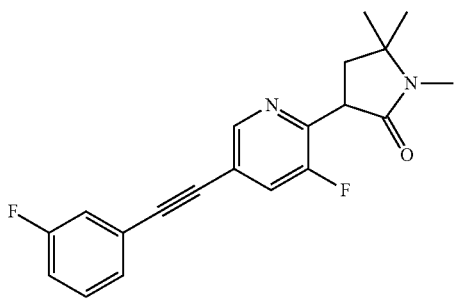

Step 1: (RS)-3-(3-Fluoro-5-iodo-pyridin-2-yl)-1,5,5-trimethyl-pyrrolidin-2-one

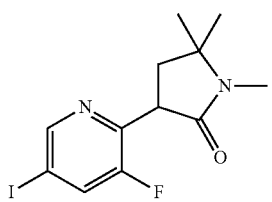 [SMILES: CN1C(=O)C(c2ncc(I)cc2F)CC1(C)C]

The title compound was obtained as a light brown solid, MS: m/e=349.0 (M+H⁺), using chemistry similar to that described in Example 1, step 1 from 2,3-difluoro-5-iodopyridine and 1,5,5-trimethyl-pyrrolidin-2-one.

Step 2: (RS)-3-(3-fluoro-5-((3-fluorophenyl)ethynyl)pyridin-2-yl)-1,5,5-trimethylpyrrolidin-2-one

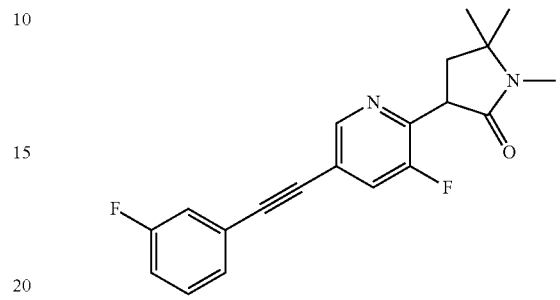

The title compound was obtained as a light brown oil, MS: m/e=319.1 (M+H⁺), using chemistry similar to that described in example 1, step 2 from (RS)-3-(3-fluoro-5-iodo-pyridin-2-yl)-1,5,5-trimethyl-pyrrolidin-2-one (Example 21, step 1) and 1-ethynyl-3-fluorobenzene.

Example 22

(RS)-1-Methyl-3-(5-phenylethynyl-pyridin-2-yl)-azepan-2-one

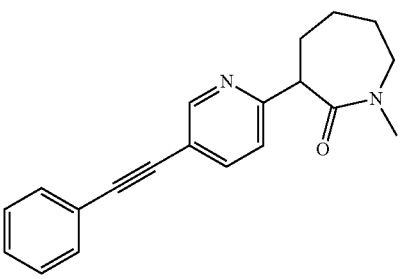 [SMILES: CN1CCCCC(c2ccc(C#Cc3ccccc3)cn2)C1=O]

Step 1: (RS)-3-(5-Iodo-pyridin-2-yl)-1-methyl-azepan-2-one

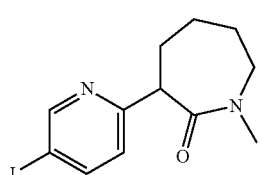

The title compound was obtained as a light yellow solid, MS: m/e=331.0 (M+H⁺), using chemistry similar to that described in Example 1, step 1 from 2-fluoro-5-iodopyridine and 1-methyl-azepan-2-one.

Step 2: (RS)-1-Methyl-3-(5-phenylethynyl-pyridin-2-yl)-azepan-2-one

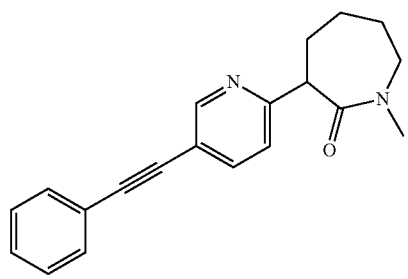 [SMILES: CN1CCCCC(c2ccc(C#Cc3ccccc3)cn2)C1=O]

The title compound was obtained as an orange solid, MS: m/e=305.1 (M+H⁺), using chemistry similar to that described in example 1, step 2 from (RS)-3-(5-iodo-pyridin-2-yl)-1-methyl-azepan-2-one (Example 22, step 1) and phenylacetylene.

Example 23

(RS)-3-[5-(4-Fluoro-phenylethynyl)-pyridin-2-yl]-1-methyl-azepan-2-one

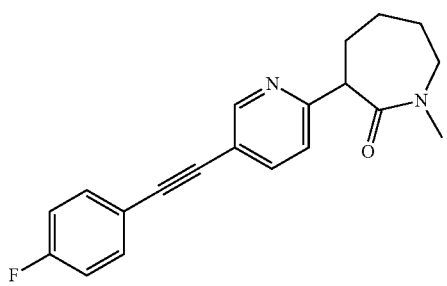 [SMILES: CN1CCCCC(c2ccc(C#Cc3ccc(F)cc3)cn2)C1=O]

The title compound was obtained as a light yellow solid, MS: m/e=323.1 (M+H⁺), using chemistry similar to that described in example 1, step 2 from (RS)-3-(5-iodo-pyridin-2-yl)-1-methyl-azepan-2-one (Example 22, step 1) and 1-ethynyl-4-fluoro-benzene.

Example 24

(RS)-3-[5-(3-Fluoro-phenylethynyl)-pyridin-2-yl]-1-methyl-azepan-2-one

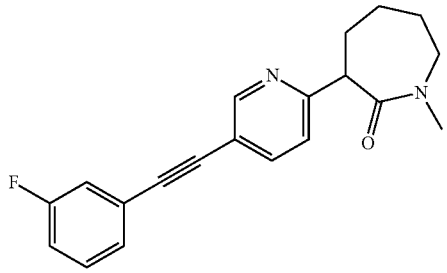 [SMILES: CN1CCCCC(c2ccc(C#Cc3cccc(F)c3)cn2)C1=O]

The title compound was obtained as a light brown solid, MS: m/e=323.1 (M+H⁺), using chemistry similar to that described in example 1, step 2 from (RS)-3-(5-iodo-pyridin-2-yl)-1-methyl-azepan-2-one (Example 22, step 1) and 1-ethynyl-3-fluoro-benzene.

Example 25

(S or R)-1-Methyl-3-(5-phenylethynyl-pyridin-2-yl)-azepan-2-one

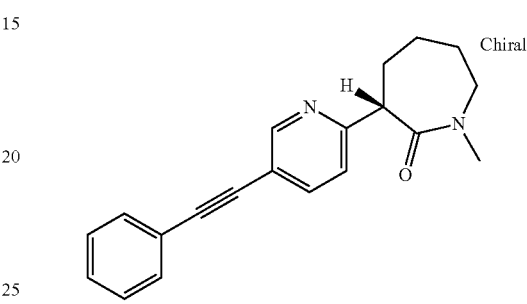

or

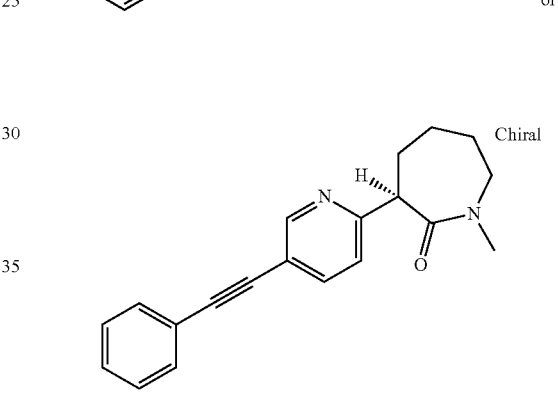

The title compound, a light yellow oil, MS: m/e=305.1 (M+H⁺), was prepared by separation of (RS)-1-methyl-3-(5-phenylethynyl-pyridin-2-yl)-azepan-2-one (Example 22) using a chiral column (Reprosil Chiral NR with heptane:ethanol 60:40 as solvent).

Example 26

(R or S)-1-Methyl-3-(5-phenylethynyl-pyridin-2-yl)-azepan-2-one

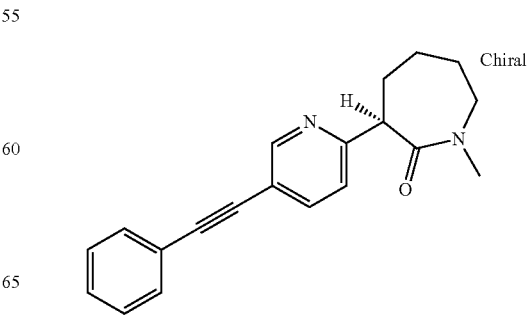

or

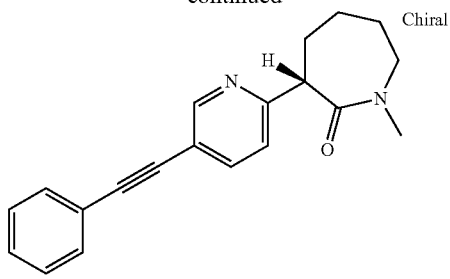

The title compound, a light yellow oil, MS: m/e=305.1 (M+H⁺), was prepared by separation of (RS)-1-methyl-3-(5-phenylethynyl-pyridin-2-yl)-azepan-2-one (Example 22) using a chiral column (Reprosil Chiral NR with heptane:ethanol 60:40 as solvent).

Example 27

(3RS,3aSR,6aSR)-1-Methyl-3-(5-phenylethynyl-pyridin-2-yl)-hexahydro-cyclopenta[b]pyrrol-2-one

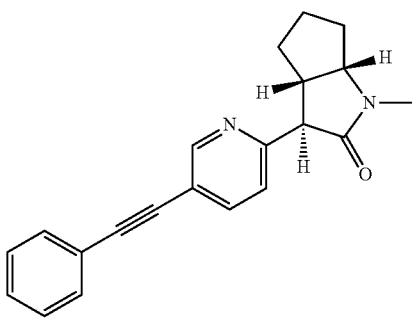 [SMILES: CN1C(=O)[C@@H](c2ccc(C#Cc3ccccc3)cn2)[C@@H]2CCC[C@@H]21]

Step 1: (3RS,3aSR,6aSR)-3-(5-Iodo-pyridin-2-yl)-1-methyl-hexahydro-cyclopenta[b]pyrrol-2-one

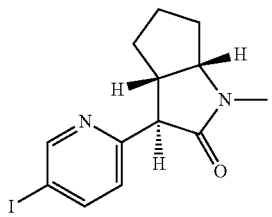 [SMILES: CN1C(=O)[C@@H](c2ccc(I)cn2)[C@@H]2CCC[C@@H]21]

The title compound was obtained as a yellow oil, MS: m/e=342.9 (M+H⁺), using chemistry similar to that described in Example 1, step 1 from 2-fluoro-5-iodopyridine and cis-1-methyl-hexahydro-cyclopenta[b]pyrrol-2-one (CAS 169688-72-6).

Step 2: (3RS,3aSR,6aSR)-1-Methyl-3-(5-phenylethynyl-pyridin-2-yl)-hexahydro-cyclopenta[b]pyrrol-2-one

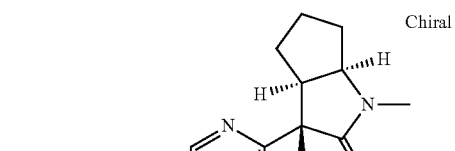

The title compound was obtained as a brown oil, MS: m/e=317.1 (M+H⁺), using chemistry similar to that described in example 1, step 2 from (3RS,3aSR,6aSR)-3-(5-iodo-pyridin-2-yl)-1-methyl-hexahydro-cyclopenta[b]pyrrol-2-one (Example 27, step 1) and phenylacetylene.

Example 28

(3R,3aS,6aS) or (3S,3aR,6aR)-1-Methyl-3-(5-phenylethynyl-pyridin-2-yl)-hexahydro-cyclopenta[b]pyrrol-2-one

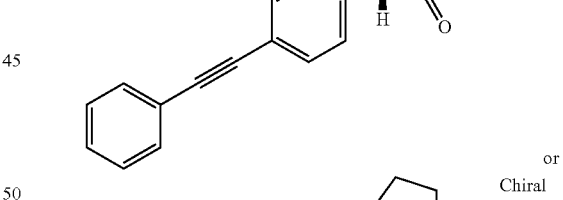

or

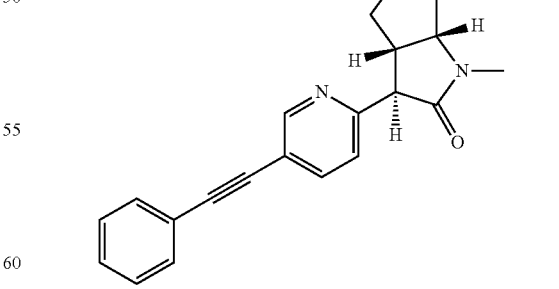

The title compound, a light yellow oil, MS: m/e=317.1 (M+H⁺), was prepared by separation of (3RS,3aSR,6aSR)-1-methyl-3-(5-phenylethynyl-pyridin-2-yl)-hexahydro-cyclopenta[b]pyrrol-2-one (Example 27) using a chiral column (Chiralpak AD with heptane:isopropanol 60:40 as solvent).

Example 29

(3RS,3aSR,6aSR)-3-[5-(4-Fluoro-phenylethynyl)-pyridin-2-yl]-1-methyl-hexahydro-cyclopenta[b]pyrrol-2-one

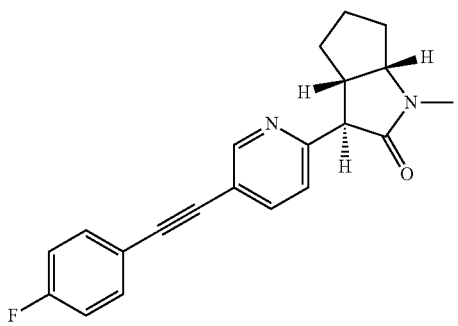 [SMILES: CN1C(=O)[C@@H](c2ccc(C#Cc3ccc(F)cc3)cn2)[C@@H]2CCC[C@@H]21]

The title compound was obtained as a light brown oil, MS: m/e=335.1 (M+H⁺), using chemistry similar to that described in example 1, step 2 from (3RS,3aSR,6aSR)-3-(5-iodo-pyridin-2-yl)-1-methyl-hexahydro-cyclopenta[b]pyrrol-2-one (Example 27, step 1) and 1-ethynyl-4-fluoro-benzene.

Example 30

(3RS,3aSR,6aSR)-3-[5-(3-Fluoro-phenylethynyl)-pyridin-2-yl]-1-methyl-hexahydro-cyclopenta[b]pyrrol-2-one

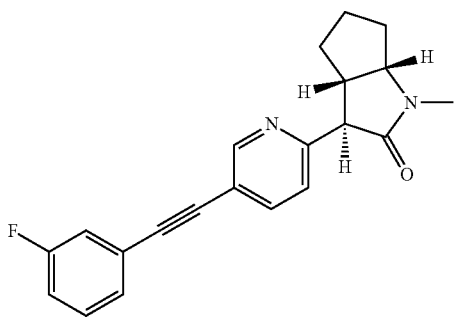 [SMILES: CN1C(=O)[C@@H](c2ccc(C#Cc3cccc(F)c3)cn2)[C@@H]2CCC[C@@H]21]

The title compound was obtained as a light brown oil, MS: m/e=335.1 (M+H⁺), using chemistry similar to that described in example 1, step 2 from (3RS,3aSR,6aSR)-3-(5-iodo-pyridin-2-yl)-1-methyl-hexahydro-cyclopenta[b]pyrrol-2-one (Example 27, step 1) and 1-ethynyl-3-fluoro-benzene.

Example 31

(3R,3aS,6aS) or (3S,3aR,6aR)-3-[5-(3-Fluoro-phenylethynyl)-pyridin-2-yl]-1-methyl-hexahydro-cyclopenta[b]pyrrol-2-one

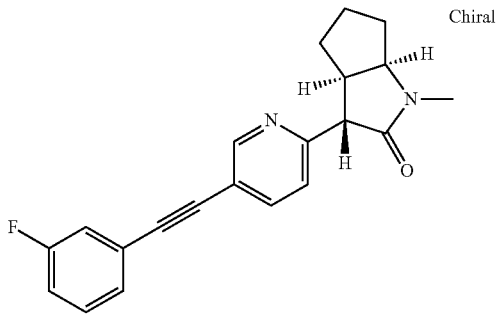

or

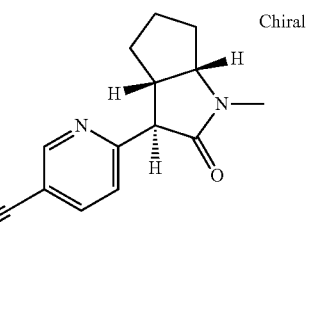

The title compound, a light yellow oil, MS: m/e=335.1 (M+H⁺), was prepared by separation of (3RS,3aSR,6aSR)-3-[5-(3-fluoro-phenylethynyl)-pyridin-2-yl]-2-methyl-hexahydro-cyclopenta[b]pyrrol-2-one (Example 30) using a chiral column (Reprosil Chiral NR with heptane:ethanol 160:40 as solvent).

Example 32

(3S,3aR,6aR) or (3R,3aS,6aS)-3-[5-(3-Fluoro-phenylethynyl)-pyridin-2-yl]-1-methyl-hexahydro-cyclopenta[b]pyrrol-2-one

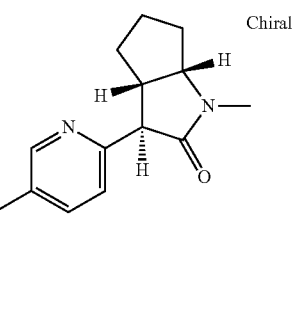

or

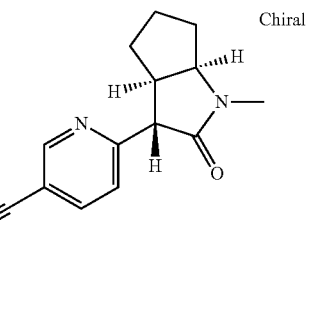

The title compound, a light yellow oil, MS: m/e=335.1 (M+H⁺), was prepared by separation of (3RS,3aSR,6aSR)-3-[5-(3-fluoro-phenylethynyl)-pyridin-2-yl]-1-methyl-hexahydro-cyclopenta[b]pyrrol-2-one (Example 30) using a chiral column (Reprosil Chiral NR with heptane:ethanol 60:40 as solvent).

Example 33

(3RS,3aSR,6aSR)-1-Methyl-3-(5-phenylethynyl-pyrimidin-2-yl)-hexahydro-cyclopenta[b]pyrrol-2-one

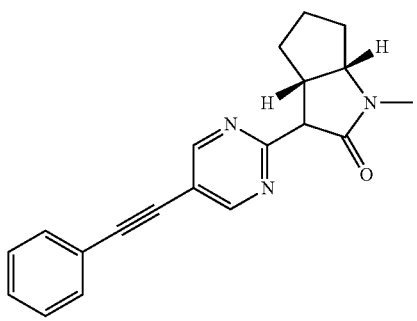 [SMILES: CN1C(=O)C(c2ncc(C#Cc3ccccc3)cn2)[C@@H]2CCC[C@@H]21]

The title compound was obtained as a white solid, MS: m/e=318.1 (M+H$^+$), using chemistry similar to that described in example 5 and example 6 starting from cis-1-methyl-hexahydro-cyclopenta[b]pyrrol-2-one (CAS 169688-72-6) instead of 5,5-dimethylpyrrolidin-2-one.

Examples 34 and 35

(3RS,6SR,7SR)-1-Methyl-3-(5-phenylethynyl-pyridin-2-yl)-octahydro-indol-2-one and (3SR,6SR,7SR)-1-Methyl-3-(5-phenylethynyl-pyridin-2-yl)-octahydro-indol-2-one

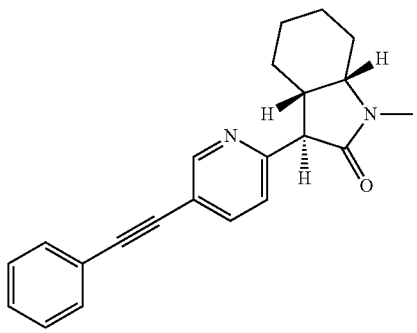

Step 1: 7:1-mixture of (3RS,5SR,6SR)-3-(5-Iodo-pyridin-2-yl)-1-methyl-octahydro-indol-2-one and (3SR,5SR,6SR)-3-(5-Iodo-pyridin-2-yl)-1-methyl-octahydro-indol-2-one

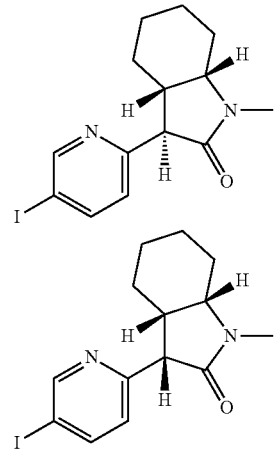

The title compound mixture was obtained as a yellow solid, MS: m/e=357.1 (M+H$^+$), using chemistry similar to that described in Example 1, step 1 from 2-fluoro-5-iodopyridine and racemic cis-octahydro-1-methyl-2H-indol-2-one (CAS 116725-60-1).

Step 2: (3RS,6SR,7SR)-1-Methyl-3-(5-phenylethynyl-pyridin-2-yl)-octahydro-indol-2-one and (3SR,6SR,7SR)-1-Methyl-3-(5-phenylethynyl-pyridin-2-yl)-octahydro-indol-2-one The title compound (3RS,6SR,7SR)-methyl-3-(5-phenylethynyl-pyridin-2-yl)-octahydro-indol-2-one (147 mg, major isomer, exo-adduct) was obtained as a light brown solid, MS: m/e=331.2 (M+H$^+$), and the minor isomer (3SR,6SR,7SR)-1-methyl-3-(5-phenylethynyl-pyridin-2-yl)-octahydro-indol-2-one (22 mg) was obtained as a brown gum, MS: m/e=331.2 (M+H$^+$), using chemistry similar to that described in example 1, step 2 from a 7:1-mixture of (3RS,6SR,7SR)-3-(5-iodo-pyridin-2-yl)-1-methyl-octahydro-indol 1-2-one and (3SR,6SR,7SR)-3-(5-iodo-pyridin-2-yl)-1-methyl-octahydro-indol-2one (Example 34, step 1) and phenylacetylene.

Example 36 and 37

(3R,6S,7S)-1-Methyl-3-(5-phenylethynyl-pyridin-2-yl)-octahydro-indol-2-one and (3S,6R,7R)-1-Methyl-3-(5-phenylethynyl-pyridin-2-yl)-octahydro-indol-2-one

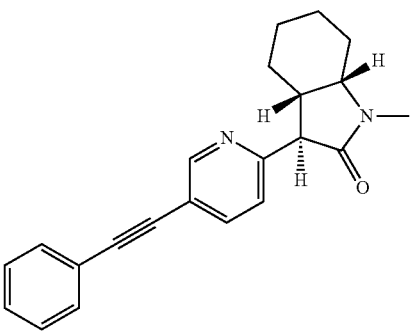

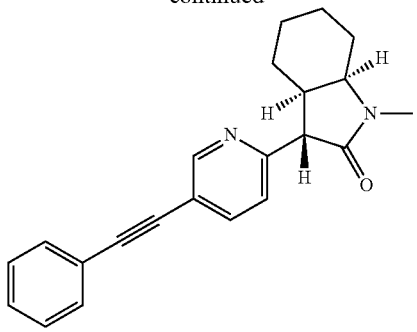

(3R,6S,7S)-1-Methyl-3-(5-phenylethynyl-pyridin-2-yl)-octahydro-indol-2-one (56 mg, colorless gum), MS: m/e=331.2 (M+H$^+$), and (3S,6R,7R)-1-methyl-3-(5-phenylethynyl-pyridin-2-yl)-octahydro-indol-2-one, (62 mg, light yellow gum), MS: m/e=331.2 (M+H$^+$), were prepared by separation of racemic (3RS,3aSR,7aSR)-1-methyl-3-(5-phenylethynyl-pyridin-2-yl)-octahydro-indol-2-one (Example 34) using a chiral column (Reprosil Chiral NR with heptane:ethanol 80:20 as solvent).

Examples 38 and 39

(3RS,6SR,7SR)-3-[5-(3-Fluoro-phenylethynyl)-pyridin-2-yl]-1-methyl-octahydro-indol-2-one and (3SR,6SR,7SR)-3-[5-(3-Fluoro-phenylethynyl)-pyridin-2-yl]-1-methyl-octahydro-indol-2-one

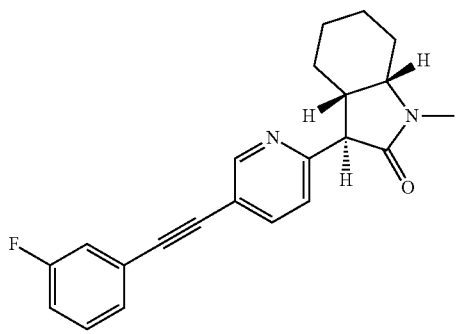

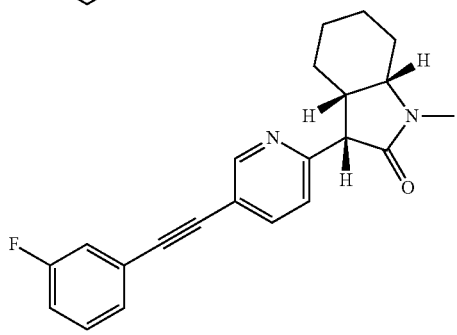

The title compound (3RS,6SR,7SR)-3-[5-(3-fluoro-phenylethynyl)-pyridin-2-yl]-1-methyl-octahydro-indol-2-one (187 mg, major isomer, exo-adduct) was obtained as a yellow oil, MS: m/e=349.3 (M+H$^+$), and the minor isomer (3SR,6SR,7SR)-3-[5-(3-fluoro-phenylethynyl)-pyridin-2-yl]-1-methyl-octahydro-indol-2-one (25 mg) was obtained as a light brown gum, MS: m/e=349.3 (M+H$^+$), using chemistry similar to that described in example 34 and 35, step 2 from a 7:1-mixture of (3RS,3aSR,7aSR)-3-(5-iodo-pyridin-2-yl)-1-methyl-octahydro-indol-2-one and (3SR,3aSR,7aSR)-3-(5-iodo-pyridin-2-yl)-1-methyl-octahydro-indol-2one (Example 34, step 1) and 3-fluorophenylacetylene.

Example 40 and 41

(3R,6S,7S)-3-[5-(3-Fluoro-phenylethynyl)-pyridin-2-yl]-1-methyl-octahydro-indol-2-one and (3S,6R,7R)-3-[45-(3-Fluoro-phenylethynyl)-pyridin-2-yl]-1-methyl-octahydro-indol-2-one

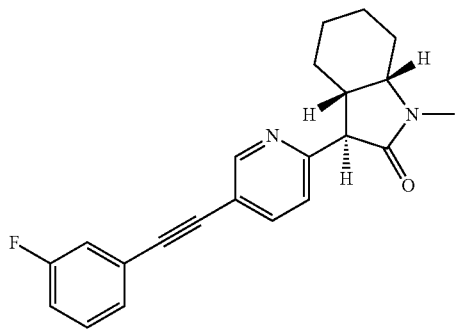

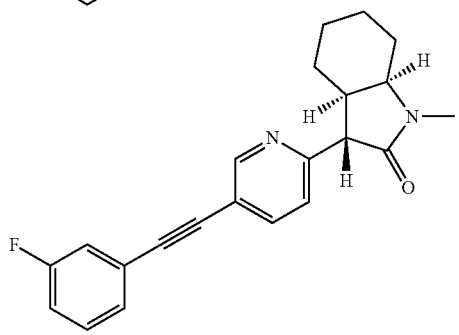

(3R,6S,7S)-3-[5-(3-fluoro-phenylethynyl)-pyridin-2-yl]-1-methyl-octahydro-indol-2-one (66 mg, colorless gum), MS: m/e=349.3 (M+H$^+$), (3S,6R,7R)-3-[5-(3-fluoro-phenylethynyl)-pyridin-2-yl]-1-methyl-octahydro-indol-2-one (63 mg, colorless gum), MS: m/e=349.3 (M+H$^+$), were prepared by separation of racemic (3RS,6SR,7SR)-3-[5-(3-fluoro-phenylethynyl)-pyridin-2-yl]-1-methyl-octahydro-indol-2-one (Example 38) using a chiral column (Reprosil Chiral NR with heptane:ethanol 60:40 as solvent).

Example 42 and 43

(3R,6S,7S)-3-[5-(4-Fluoro-phenylethynyl)-pyridin-2-yl]-1-methyl-octahydro-indol-2-one and (3 S,6R,7R)-3-[5-(4-Fluoro-phenylethynyl)-pyridin-2-yl]-1-methyl-octahydro-indol-2-one

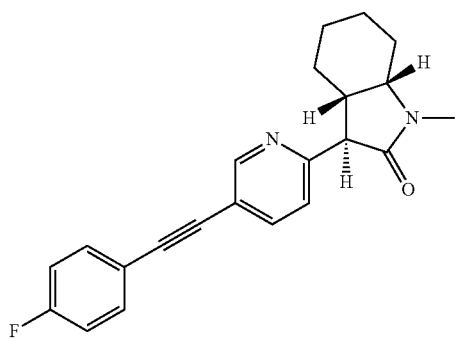

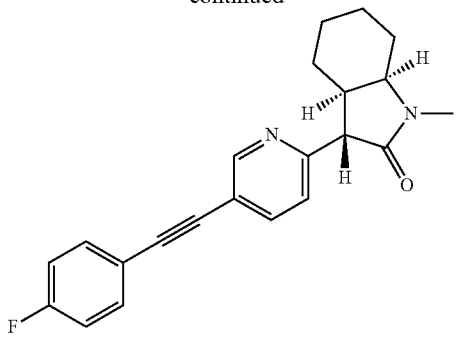

Step 1: (3RS,6SR,7SR)-3-[5-(4-Fluoro-phenylethynyl)-pyridin-2-yl]-1-methyl-octahydro-indol-2-one§

The title compound, racemic (3RS,6SR,7SR)-3-[5-(4-fluoro-phenylethynyl)-pyridin-2-yl]-1-methyl-octahydro-indol-2-one (189 mg, major isomer, exo-adduct) was obtained as a light brown oil, MS: m/e=349.3 (M+H⁺), using chemistry similar to that described in example 34, step 2 from a 7:1-mixture of (3RS,3aSR,7aSR)-3-(5-iodo-pyridin-2-yl)-1-methyl-octahydro-indol-2-one and (3SR,3aSR,7aSR)-3-(5-iodo-pyridin-2-yl)-1-methyl-octahydro-indol-2one (Example 34, step 1) and 4-fluorophenylacetylene. The minor isomer was not isolated.

(3R,6S,7S)-3-[5-(4-Fluoro-phenylethynyl)-pyridin-2-yl]-1-methyl-octahydro-indol-2-one (78 mg, light yellow gum), MS: m/e=349.3 (M+H⁺), (3S,6R,7R)-3-[5-(4-fluoro-phenylethynyl)-pyridin-2-yl]-1-methyl-octahydro-indol-2-one (75 mg, light yellow gum), MS: m/e=349.3 (M+H⁺), were prepared by separation of racemic (3RS,6SR,7SR)-3-[5-(4-fluoro-phenylethynyl)-pyridin-2-yl]-1-methyl-octahydro-indol-2-one (Example 42) using a chiral column (Reprosil Chiral NR with heptane:ethanol 60:40 as solvent).

Example 44

(RS)-3-[5-(2-Chloro-pyridin-4-ylethynyl)-pyridin-2-yl]-1,5,5-trimethyl-pyrrolidin-2-one

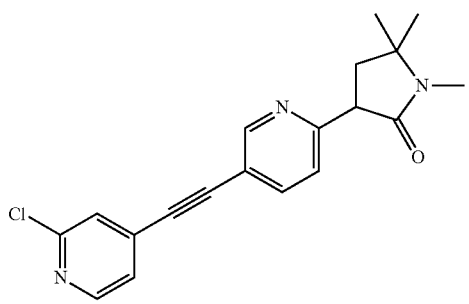 [SMILES: CN1C(=O)C(c2ccc(C#Cc3ccnc(Cl)c3)cn2)CC1(C)C]

The title compound was obtained as a light yellow oil, MS: m/e=340.3/342.4 (M+H⁺), using chemistry similar to that described in Example 1, step 2 from (RS)-3-(5-iodopyridin-2-yl)-1,5,5-trimethylpyrrolidin-2-one (Example 1, step 1) and 2-chloro-4-ethynyl-pyridine (CAS 945717-09-9).

Example 45

(S) or (R)-3-[5-(2-Chloro-pyridin-4-ylethynyl)-pyridin-2-yl]-1,5,5-trimethyl-pyrrolidin-2-one

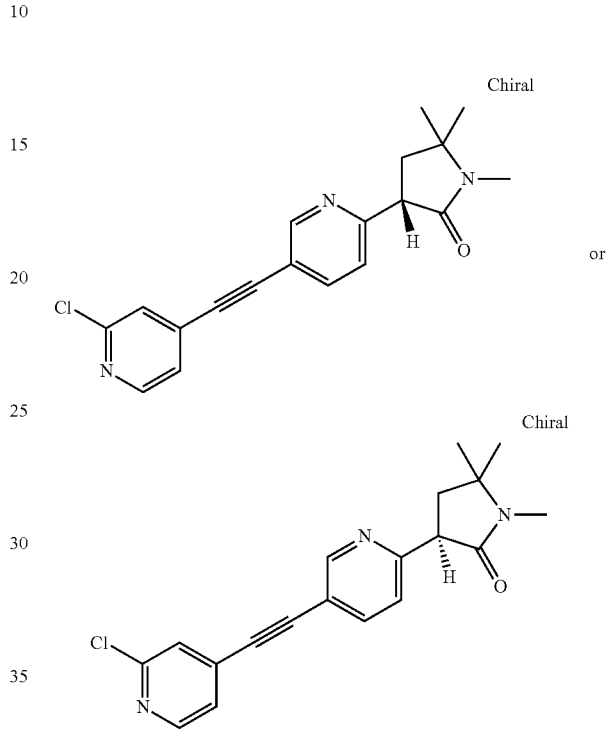

The title compound, a yellow solid, MS: m/e=340.4/342.4 (M+H⁺), was prepared by separation of (RS)-3-[5-(2-chloro-pyridin-4-ylethynyl)-pyridin-2-yl]-1,5,5-trimethyl-pyrrolidin-2-one (Example 44) using a chiral column (Chiralpak AD with heptane:isopropanol 60:40 as solvent).

Example 46

(R) or (S)-3-[5-(2-Chloro-pyridin-4-ylethynyl)-pyridin-2-yl]-1,5,5-trimethyl-pyrrolidin-2-one

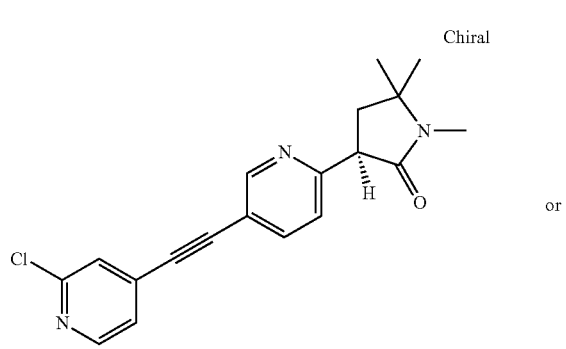

-continued

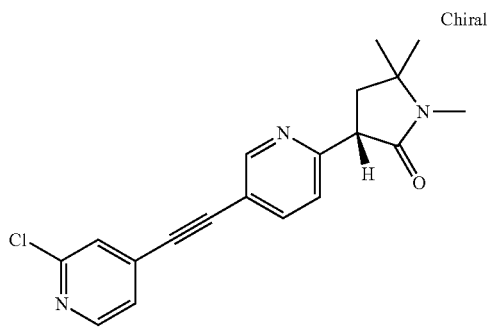

The title compound, a light yellow solid, MS: m/e=340.4/342.4 (M+H⁺), was prepared by separation of (RS)-3-[5-(2-chloro-pyridin-4-ylethynyl)-pyridin-2-yl]-1,5,5-trimethyl-pyrrolidin-2-one (Example 44) using a chiral column (Chiralpak AD with heptane:isopropanol 60:40 as solvent).

The invention claimed is:

1. A compound of formula

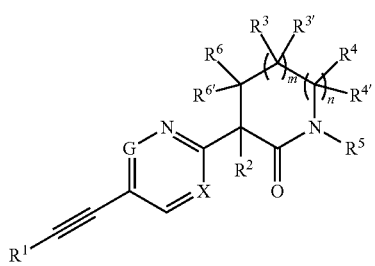

I wherein
X is N;
G is CH;
$R^1$ is phenyl or pyridinyl, each of which is optionally substituted by halogen;
$R^2$ is hydrogen, lower alkyl, hydroxy, lower alkoxy or C(O)O-benzyl;
$R^3$, $R^{3'}$, $R^4$, $R^{4'}$, $R^6$, and $R^{6'}$ are each independently hydrogen or lower alkyl;
or $R^6$ and $R^4$ together with the carbon atom to which they are attached form a $C_{4-6}$-cycloalkyl ring, when m is 0 and n is 1 or 2;
$R^5$ is hydrogen or lower alkyl;
n is 0, 1 or 2; and
m is 0 or 1; with the proviso that n and m are not simultaneously 0;
or a pharmaceutically acceptable acid addition salt, a racemic mixture, its corresponding enantiomer or stereoisomer thereof.

2. The compound of claim 1, having formula IB

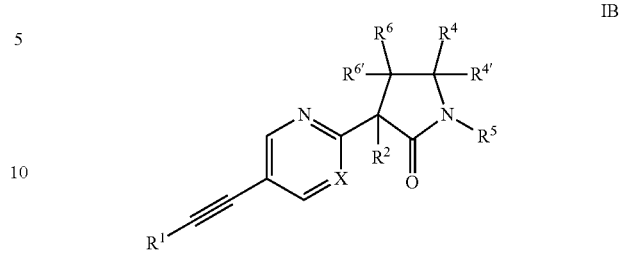

IB wherein
X is N;
$R^1$ is phenyl or pyridinyl, each of which is optionally substituted by halogen;
$R^2$ is hydrogen, lower alkyl, hydroxy, lower alkoxy or C(O)O-benzyl;
$R^4$, $R^{4'}$, $R^6$, and $R^{6'}$ are each independently hydrogen or lower alkyl;
or $R^6$ and $R^4$ together with the carbon atom to which they are attached form a $C_{4-6}$-cycloalkyl ring; and
$R^5$ is hydrogen or lower alkyl;
or a pharmaceutically acceptable acid addition salt, a racemic mixture, its corresponding enantiomer or stereoisomer thereof.

3. A compound of claim 2, selected from the group consisting of
(RS)-benzyl 1,5,5-trimethyl-2-oxo-3-(5-(phenylethynyl)pyrimidin-2-yl)pyrrolidine-3-carboxylate;
(RS)-1,5,5-trimethyl-3-(5-(phenylethynyl)pyrimidin-2-yl)pyrrolidin-2-one;
(RS)-3-(5-((3-fluorophenyl)ethynyl)pyrimidin-2-yl)-1,5,5-trimethylpyrrolidin-2-one;
(RS)-3-(5-((4-fluorophenyl)ethynyl)pyrimidin-2-yl)-1,5,5-trimethylpyrrolidin-2-one; and
(3RS,3aSR,6aSR)-1-methyl-3-(5-phenylethynyl-pyrimidin-2-yl)-hexahydro-cyclopenta[b]pyrrol-2-one.

4. The compound of claim 1, having formula IE

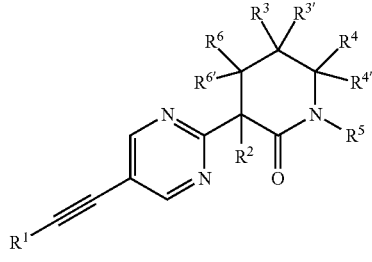

IE wherein
$R^1$ is phenyl or pyridinyl, each of which is optionally substituted by halogen;
$R^2$ is hydrogen, lower alkyl, hydroxy, lower alkoxy or C(O)O-benzyl;
$R^3$, $R^{3'}$, $R^4$, $R^{4'}$, $R^6$, and $R^{6'}$ are each independently hydrogen or lower alkyl; and
$R^5$ is hydrogen or lower alkyl;
or a pharmaceutically acceptable acid addition salt, a racemic mixture, its corresponding enantiomer or stereoisomer thereof.

5. The compound of claim 4, selected from the group consisting of
(RS)-1,6,6-trimethyl-3-(5-(phenylethynyl)pyrimidin-2-yl)piperidin-2-one;
(RS)-3-(5-((4-fluorophenyl)ethynyl)pyrimidin-2-yl)-1,6,6-trimethylpiperidin-2-one; and
(RS)-3-(5-((3-fluorophenyl)ethynyl)pyrimidin-2-yl)-1,6,6-trimethylpiperidin-2-one.

6. A pharmaceutical composition comprising a therapeutically effective amount of a compound of formula I

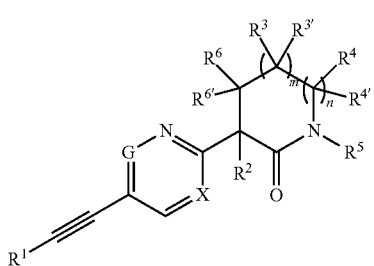

wherein
X is N;
G is CH;
$R^1$ is phenyl or pyridinyl, each of which is optionally substituted by halogen;
$R^2$ is hydrogen, lower alkyl, hydroxy, lower alkoxy or C(O)O-benzyl;
$R^3$, $R^{3'}$, $R^4$, $R^{4'}$, $R^6$, and $R^{6'}$ are each independently hydrogen or lower alkyl;
or $R^6$ and $R^4$ together with the carbon atom to which they are attached form a $C_{4-6}$-cycloalkyl ring, when m is 0 and n is 1 or 2;
$R^5$ is hydrogen or lower alkyl;
n is 0, 1 or 2; and
m is 0 or 1; with the proviso that n and m are not simultaneously 0;
or a pharmaceutically acceptable acid addition salt, a racemic mixture, its corresponding enantiomer or stereoisomer thereof,
and a pharmaceutically acceptable excipient.

* * * * *